US007829687B2

(12) United States Patent
Georgiou et al.

(10) Patent No.: US 7,829,687 B2
(45) Date of Patent: Nov. 9, 2010

(54) ARTIFICIAL DISULFIDE ISOMERASES AND USES THEREOF

(75) Inventors: George Georgiou, Austin, TX (US); Laura Segatori, Houston, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 627 days.

(21) Appl. No.: 11/697,114

(22) Filed: Apr. 5, 2007

(65) Prior Publication Data

US 2007/0243583 A1 Oct. 18, 2007

Related U.S. Application Data

(60) Provisional application No. 60/790,522, filed on Apr. 7, 2006.

(51) Int. Cl.
| | |
|---|---|
| C07H 21/04 | (2006.01) |
| C12N 15/00 | (2006.01) |
| C12N 1/20 | (2006.01) |
| C12N 1/00 | (2006.01) |
| C12N 5/00 | (2006.01) |
| C12N 5/02 | (2006.01) |
| C12P 21/04 | (2006.01) |

(52) U.S. Cl. .................. 536/23.4; 536/23.7; 435/320.1; 435/252.3; 435/252.33; 435/254.11; 435/254.2; 435/325; 435/70.1; 435/71.1

(58) Field of Classification Search ........................ None
See application file for complete search history.

(56) References Cited

U.S. PATENT DOCUMENTS

| | | | | |
|---|---|---|---|---|
| 5,639,635 A | 6/1997 | Joly et al. | ................... | 435/69.1 |
| 5,789,199 A | 8/1998 | Joly et al. | ................... | 435/69.1 |
| 6,083,715 A | 7/2000 | Georgiou et al. | ........... | 435/69.1 |

OTHER PUBLICATIONS

Branden et al. "Introduction to Protein Structure Second Edition," Garland Publishings Inc., New York 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Martin et al. (Crystal structure of the DsbA protein required for disulphide bond formation in vivo, Nature. Sep. 30, 1993; 365 (6445): 464-8).*
PCT International Search Report and Written Opinion, issued in International Application PCT/US2007/066086, dated Oct. 25, 2007.
Arie et al., "Chaperone function of FkpA, a heat shock prolyl isomerase, in the periplasm of *Escherichia coli*," *Mol. Microbiol.*, 39:199-210, 2001.
Baneyx and Georgiou, "In vivo degradation of secreted fusion proteins by the *Escherichia coli* outer membrane protease OmpT," *J. Bacteriol.*, 172:491-494, 1990.
Baneyx and Mujacic, "Recombinant protein folding and misfolding in *Escherichia coli*," *Nat. Biotechnol.*, 22:1399-1408, 2004.
Bardwell et al., "A pathway for disulfide bond formation in vivo," *Pro. Nat. Acad. Sci. USA*, 90:1038-1042, 1993.
Bardwell et al., "Building bridges: disulphide bond formation in the cell," *Mol. Microbiol.*, 14:199-205, 1994.
Behrens et al., "The SurA periplasmic PPIase lacking its parvulin domains functions in vivo and has chaperone activity," *EMBO J.*, 20:285-294, 2001.
Berkmen et al., "The nonconsecutive disulfide bond of *Escherichia coli* phytase (AppA) renders it dependent on the protein-disulfide isomerase, DsbC," *J. Biol. Chem.*, 280:11387-11394, 2005.
Collet and Bardwell, "Oxidative protein folding in bacteria," *Mol. Microbiol.*, 44:1-8, 2002.
Database WPI Week 200513 Derwent Publications Ltd., London, GB; AN 2005-115299 & JP 2005 013066 A (Sekisui Chem Ind Co Ltd) Jan. 20, 2005.
Hiniker et al., "Copper stress causes an in vivo requirement for the *Escherichia coli* disulfide isomerase DsbC," *J. Biol. Chem.*, 280:33785-33791, 2005.
Joly et al., "Overexpression of *Escherichia coli* oxidoreductases increases recombinant insulin-like growth factor-I accumlation," *Proc. Natl. Acad. Sci. USA*, 95:2773-2777, 1998.
Kadokura et al., "Protein disulfide bond formation in prokaryotes," *Annu. Rev. Biochem.*, 72:111-135, 2003.
Kim and Swartz, "Efficient production of a bioactive, multiple disulfide-bonded protein using modified extracts of *Escherichia coli*," *Biotechnol. Bioeng.*, 85:122-129, 2004.
Kurokawa et al., "Overproduction of bacterial protein disulfide isomerase (DsbC) and its modulator (DsbD) markedly enhances periplasmic production of human nerve growth factor in *Escherichia coli*," *J Biol. Chem.*, 276:14393-14399, 2001.
Missiakas et al., "The *Escherichia coli* dsbC (xprA) gene encodes a periplasmic protein involved in disulfide bond formation," *EMBO J.*, 13:2013-2020, 1994.
Ramm and Pluckthun, "High enzymatic activity and chaperone function are mechanistically related features of the dimeric E. coli peptidyl-prolyl-isomerase FkpA," *J. Mol. Biol.*, 310:485-498, 2001.
Rozhkova et al., "Structural basis and kinetics of inter- and intramolecular disulfide exchange in the redox catalyst DsbD," *Embo. J.*, 23:1709-1719, 2004.
Saul et al., "Structural and functional studies of FkpA from *Escherichia coli*, a cis/trans Peptidyl-prolyl Isomerase with Chaperone Activity," *J Mol. Biol.*, 335:595-608, 2004.
Segatori "Structure, function, and engineering of disulfide bond isomerisation in *Escherichia coli*," Dissertation, The University of Texas at Austin, 2005.
Segatori et al., "Engineered DsbC chimeras catalyze both protein oxidation and disulfide-bond isomerization in *Escherichia coli*: Reconciling two competing pathways," *Proc. Natl. Acad. Sci. USA*, 101:10018-10023, 2004.
Zapun et al., "Structural and functional characterization of DsbC, a protein involved in disulfide bond formation in *Escherichia coli*," *Biochemistry*, 34:5075-5089, 1995.
Zapun et al., "The reactive and destabilizing disulfide bond of DsbA, a protein required for protein disulfide bond formation in vivo," *Biochemistry*, 32:5083-5092, 1993.
Zhao et al., "Dimerization by domain hybridization bestows chaperone and isomerase activities," *J. Biol. Chem.*, 278:43292-43298, 2003.

\* cited by examiner

*Primary Examiner*—Suzanne M Noakes
*Assistant Examiner*—Jae W Lee
(74) *Attorney, Agent, or Firm*—Fulbright & Jaworski L.L.P.

(57) ABSTRACT

The present invention provides artificial enzymes comprising, e.g., an N-terminal domain derived from *E. coli* FkpA that allows for dimerization and provides a substrate binding region, and a C-terminal thioredoxin domain derived from *E. coli* DsbA. Similar to DsbC, such de novo designed chimeric (hybrid) FkpA-DsbA enzymes function, as disulfide reductases, oxidases, or isomerases, and chaperones in vivo and in vitro, despite lacking similarity to DsbC-related polypeptide sequence.

21 Claims, 3 Drawing Sheets

US 7,829,687 B2

ARTIFICIAL DISULFIDE ISOMERASES AND USES THEREOF

The present application claims priority to U.S. patent application Ser. No. 60/790,522 filed Apr. 7, 2006, the entire text of which is specifically incorporated by reference herein without disclaimer.

This invention was made with government support under grant number GM055090 awarded by the National Institutes of Health. The government has certain rights in the invention.

BACKGROUND OF THE INVENTION

1. Field of the Invention

The invention generally concerns the field of molecular biology. More specifically, the invention relates to methods and compositions for efficient expression of polypeptides comprising disulfide linkages.

2. Description of Related Art

Oxidative protein folding involves two complementary but competing processes: cysteine thiol oxidation, and isomerization of non-native disulfide bonds. The limiting step in the folding of multi disulfide eukaryotic proteins in the bacterial periplasm is often the isomerization of non-native disulfides.

The bacterial disulfide bond formation ("Dsb") protein family consists of two distinct pathways, DsbA-DsbB, and DsbC/DsbG-DsbD, involved in the formation of disulfides and in the rearrangement of incorrectly formed bonds, respectively (Kadokura et al., 2003; Collet and Bardwell, 2002). The extreme oxidizing nature of mature DsbA (SEQ ID NO:3) mediates rapid oxidation of substrate cysteines, which results in the formation of non-native disulfides, in turn rearranged by DsbC. Consequently, despite the strong oxidizing environment of the periplasmic space, DsbC has to be maintained in a reduced state to interact with the substrate oxidized cysteines (Kadokura et al., 2003; Collet and Bardwell, 2002). To carry on their catalytic activities, DsbA and DsbC are maintained, respectively, in entirely oxidized and reduced states (Ramm and Pluckthun, 2001). DsbA is recycled by the membrane protein DsbB, whereas DsbC is maintained in the reduced state by the membrane protein, DsbD (Arie et al., 2001). Interactions between the two pathways are strongly prevented by kinetic constraints (Rozhkova et al., 2004). As a result, the strong thiol oxidant DsbA, and the strong thiol reductant DsbC, despite coexisting in the same cellular environment, do not appear to exchange electrons with each other, but instead act synergistically during oxidative protein folding. Remarkably, the catalytic domains of DsbC and DsbA show a considerable degree of structural homology, and they both contain a CXXC thioredoxin active site motif for the catalysis of disulfide exchange reactions.

The folding of at least three native proteins, namely the periplasmic acid phosphatase AppA or phytase, the peptidoglycan amidase MepA, and RNase I have been shown to depend on the presence of DsbC (Berkmen et al., 2005). In addition, the folding of a number of heterologous proteins has been shown to require overexpression of DsbC (Kadokura et al., 2003; Collet and Bardwell, 2002; Kim et al., 2004; Kurokawa et al., 2001). It was previously shown that the yield of active vtPA, a truncated version of human tissue plasminogen activator containing 9 disulfide bonds, depends on the DsbC expression level (Qiu et al., 1998).

Zhao et al. (2003) created several engineered polypeptides containing an N-terminal DsbC domain joined to a C-terminal domain from thioredoxin (Trx), DsbA, or portions of protein-disulfide isomerase (PDI). These polypeptides displayed limited isomerase and reductase activities while retaining DsbC-related sequences. It was suggested that the basis of the catalytic activity of DsbC resides in its V-shaped dimeric structure, which allows for the formation of a hydrophobic substrate binding cleft with chaperone activity, and in the presence of two catalytic thioredoxin domains (Segatori et al., 2004). The hybrid DsbC-DsbA or DsbC-TrxA polypeptides described in Segatori et al., 2004, in which the catalytic domain of DsbC had been replaced with DsbA, also displayed disulfide bond formation and isomerase activity, and afforded vtPA yields comparable to those obtained when overexpressing wild-type DsbC under the same conditions. However, the chimeric proteins of Zhao et al. and Segatori et al. each retain DsbC-derived sequences.

The *E. coli* periplasm contains two classes of enzymes that assist the folding of proteins by catalyzing covalent modification: enzymes that catalyze the reduction and oxidation of disulfide bonds (the Dsb family), and enzymes that catalyze cis/trans peptidyl-prolyl isomerization reactions (PPIases) (Baneyx and Mujacic, 2004). Among the PPIases (E.C. 5.2.1.8), which include SurA (Behrens et al., 2001) and the FK506 binding proteins (FKBP's), an FkpA (e.g., GenBank L28082) has been recently biochemically characterized, and its crystal structure has been solved (Saul et al., 2004). FkpA is a homodimeric V-shaped protein (e.g., FIG. 1) which exhibits a similar gross topology to DsbC. Each monomer in FkpA is formed by an N-terminal dimerization domain and a C-terminal catalytic domain, joined by a long α-helical linker. The two domains are each structurally and functionally independent. The dimerization domains form a binding pocket for the interaction with the substrate, and have been shown to have chaperone activity (Saul et al., 2004; Ramm and Pluckthun, 2001; Arie et al., 2001). FkpA and DsbC lack substantial amino acid sequence identity (e.g., using BLAST with default parameters). There exists a need for methods to catalyze disulfide bond formation and isomerization in bacteria without the expression of a DsbC-containing protein.

SUMMARY OF THE INVENTION

The present invention provides, in one embodiment, an engineered polypeptide lacking substantial amino acid sequence identity with DsbC that is nonetheless capable of catalyzing disulfide bond formation, disulfide bond isomerization, and/or chaperone activity in bacteria. In one aspect, the invention provides an isolated nucleic acid molecule encoding a chimeric polypeptide comprising a first DNA segment encoding an N-terminal domain derived from the N-terminal domain of a chaperone that has a V-shaped substrate binding cleft; and a second DNA segment encoding a C-terminal domain comprising DsbA or TrxA; wherein the first and second DNA segments are linked 5' to 3', and wherein the chimeric polypeptide comprises one or more activities selected from the group consisting of disulfide bond reduction activity, disulfide bond oxidation activity, disulfide bond isomerization activity, and chaperone activity. In one embodiment, the N-terminal chaperone domain is the N-terminal domain of an FkpA or an FkpA derivative, wherein the FkpA derivative allows for dimerization and provides a substrate binding region and has from about 80% to about 99% sequence identity with a wild-type FkpA. In a further embodiment, the N-terminal domain comprises residues 1-114 of FkpA. In a particular embodiment, the first DNA segment encodes a polypeptide comprising SEQ ID NO:2 or a protein fragment of a gene selected from the group consisting of GenBank Accession Number AAN44828, GenBank Accession Number AAL22316, and GenBank Accession Number L28082; wherein the protein fragment allows for dimerization and provides a substrate binding region. The second DNA segment may encode a polypeptide comprising DsbA. In certain embodiments, the second DNA segment encodes a polypeptide comprising SEQ ID NO:3, GenBank Accession Number YP_081862, or GenBank Accession Number U84726.

In another embodiment, the second DNA segment encodes a C-terminal domain comprising a DsbA polypeptide. In yet other embodiments, the encoded chimeric polypeptide comprises a sequence selected from the group consisting of SEQ ID NO:4 to SEQ ID NO:8. In various embodiments, the chaperone is not DsbC.

In another aspect, the invention provides an expression construct comprising a nucleic acid molecule that encodes a chimeric polypeptide comprising a first DNA segment encoding an N-terminal domain derived from the N-terminal domain of a chaperone that has a V-shaped substrate binding cleft; and a second DNA segment encoding a C-terminal domain comprising DsbA; wherein the first and second DNA segments are linked 5' to 3', and the chimeric polypeptide comprises one or more activities selected from the group consisting of disulfide bond reduction activity, disulfide bond oxidation activity, disulfide bond isomerization activity, and chaperone activity; and a DNA segment encoding a polypeptide comprising at least two disulfide bonds. In certain embodiments the nucleic acid molecule that encodes a chimeric polypeptide comprises a sequence selected from the group consisting of SEQ ID NO:11-SEQ ID NO:15.

In yet another aspect, the invention provides a host cell comprising a nucleic acid molecule encoding a chimeric polypeptide comprising a first DNA segment encoding an N-terminal domain derived from the N-terminal domain of a chaperone that has a V-shaped substrate binding cleft; and a second DNA segment encoding a C-terminal domain comprising DsbA; wherein the first and second DNA segments are linked 5' to 3', and the chimeric polypeptide comprises one or more activities selected from the group consisting of disulfide bond reduction activity, disulfide bond oxidation activity, disulfide bond isomerization activity, and chaperone activity. In one embodiment, the host cell is a gram negative or a gram positive bacterial cell. In a particular embodiment, the host cell of is a gram-negative bacterial cell, such as an *Escherichia coli* cell. The host cell may express at least one of DsbD and DsbB.

In yet another aspect, the invention provides a method for producing a biologically active heterologous polypeptide in a host cell comprising: a) culturing host cells in a culture medium, wherein the host cells comprise both a nucleic acid molecule encoding the chimeric polypeptide as described above, and a second nucleic acid molecule that encodes a heterologous polypeptide which comprises at least two disulfide bonds in its native form; b) expressing the nucleic acid molecule and the second nucleic acid molecule in the host cells under conditions effective to produce the chimeric polypeptide and the heterologous polypeptide; and c) isolating the heterologous polypeptide. In certain embodiments, the heterologous polypeptide is selected from the group consisting of human tPA; vtPA, RNAse A, and PhoA. In one embodiment of the method, the host cells are bacterial cells. In certain embodiments, the bacterial cells express DsbD and DsbB. In another embodiment, the bacterial cells are gram-negative bacterial cells. In a particular embodiment, the bacterial cells are *E. coli* cells. In yet another embodiment, at least one of the chimeric polypeptide and the heterologous polypeptide are operatively linked to a signal sequence that functions to cause secretion of the polypeptides from the host cell cytoplasm. The signal sequence may comprise OmpA, Lpp, LamB, MalE, PelB, or StII. The nucleic acid molecule encoding the chimeric polypeptide and the second nucleic acid molecule may be expressed by a single host cell or by separate host cells. In yet another embodiment of the method, the heterologous polypeptide is isolated from the culture medium of the host cells.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or " unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

Figure 1:
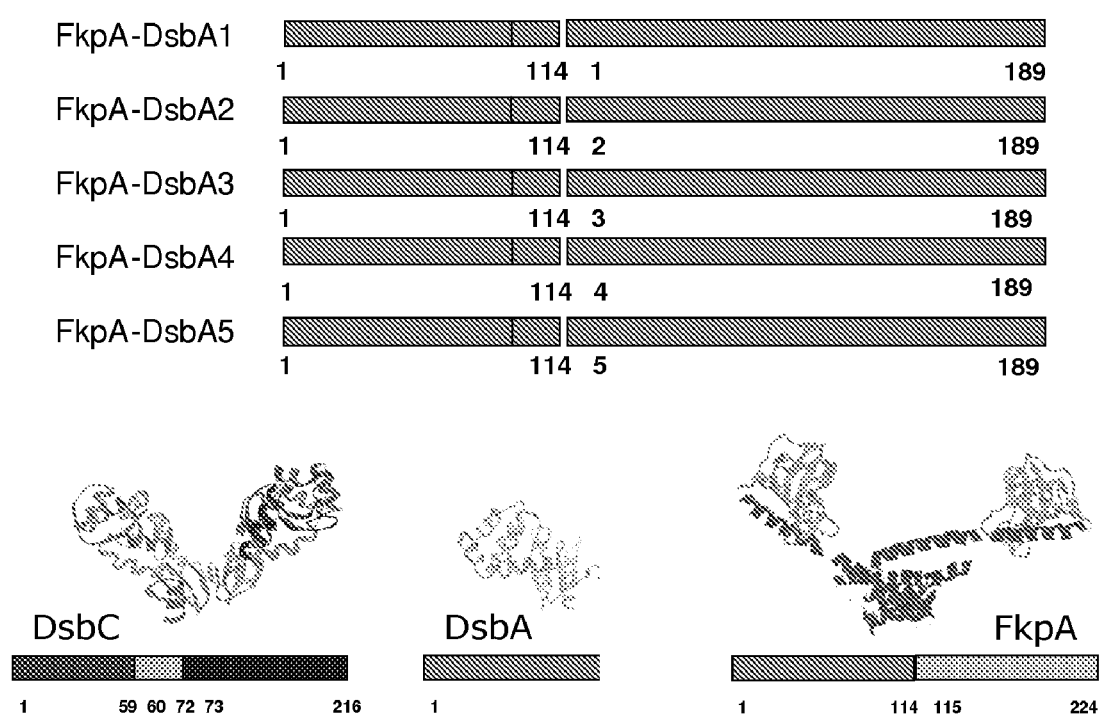
FIG. 1 Schematic representation of DsbC, DsbA, and FkpA, and domain composition of the FkpA-DsbA chimera polypeptides.

The folding of multi-disulfide containing proteins in the periplasm of E. coli occurs through the rapid, non-specific oxidation of cysteines by DsbA, and is limited by the need for subsequent isomerization of non-native disulfides (Berkmen et al., 2005; Zapun et al., 1993). To overcome this limitation, the present invention provides, in specific embodiments, artificial disulfide isomerases that: (1) can catalyze the folding of multi-disulfide proteins expressed in bacteria or other organisms and (2) comprise unique amino acid sequences that that form proteins not found in any naturally occurring disulfide isomerase.

The present invention describes the construction of artificial enzymes comprising an N-terminal domain derived from FkpA that allows for dimerization and provides a substrate binding region, and a C-terminal thioredoxin domain derived from DsbA. The ability of such chimeric (hybrid) designed enzymes to function as disulfide isomerases in vivo, and their in vitro characterization, was demonstrated. The work described below shows that FkpA-DsbA chimeras, although lacking any DsbC sequences, result in vtPA yields comparable to those provided by wild-type DsbC. In particular, FkpA-DsbA2, FkpA-DsbA3, and FkpA-DsbA4 supported the folding of vtPA with yields 80, 55, and 67% of the yield of active protein obtained with wild-type DsbC (FIG. 2A). In addition, only background levels of active vtPA were detected in cells lacking DsbD, and expressing any of the FkpA-DsbA chimeras. Without being bound by any theory, this suggests that the activity of the chimera proteins depends on their recycling by DsbD and leads to the rearrangement of non-native disulfide bonds.

Definitions:

As used herein, "dsbA" refers to a gene encoding the bacterial periplasmic protein known in the literature as DsbA. In one embodiment, the dsbA gene may comprise a sequence encoding the mature DsbA polypeptide of SEQ ID NO:3. A DsbA homolog may also be used in a chimeric protein of the present invention. Homologs of such genes are known from numerous bacterial sources, both gram-positive and gram-negative, including members of the Bacillaceae (e.g., GenBank YP_081862), Enterobacteriaceae (e.g., Shevchik et al., 1995), Pseudomonadaceae (e.g., Kloek et al., 2000; GenBank U84726), Anaplasmataceae (e.g., McBride et al., 2002), and others. In certain embodiments, chimeric proteins of the present invention may comprise a DsbA fragment comprising a C-terminal thioredoxin domain and/or thioredoxin activity. In various embodiments, a variant of a DsbA protein may be used with the present invention; for example, a chimeric protein of the present invention may comprise a DsbA derivative, wherein the DsbA derivative has thioredoxin activity and exhibits about 70, 75, 81, 85, 90, 91, 92, 93, 94, 95, 96, 97, 98, 99, 99.5, or about 99.9 percent sequence identity with a wild-type DsbA amino acid sequence.

As used herein, "fkpA" refers to a gene encoding an FK506 binding protein (FKBP) PPIase (with chaperone activity) known in the literature as FkpA (e.g., SEQ ID NO:1). A FkpA homolog or a FkpA homolog fragment may also be used in a chimeric protein of the present invention. Homologs of such FKBP genes are known from numerous bacterial sources, including members of the Enterobacteriaceae (e.g., GenBank AAN44828; AAL22316) Pseudomonadaceae (e.g., Isaki et al., 1990) Corynebacteraceae (e.g., GenBank BX927150), and others. As noted, these genes may be isolated from any bacterial source, for example the dsbA gene from *E. coli* as described in Collet and Bardwell (2002); or the fkpA gene described in Horne et al. (1995; GenBank accession L28082), or Arie et al. (2001), encoding a bacterial periplasmic protein. Variants of genes encoding functional DsbA or FkpA proteins are also contemplated. In certain embodiments, chimeric proteins of the present invention may comprise a FkpA fragment, wherein the FkpA fragment comprises a substrate binding region and allows for dimerization. In various embodiments, a variant of a FkpA protein may be used with the present invention; for example, a chimeric protein of the present invention may comprise a fragment of a FkpA derivative, wherein the fragment of a FkpA derivative has substrate binding activity, allows for dimerization, and displays about 70, 75, 81, 85, 90, 91, 92, 93, 94, 95, 96, 97, 98, 99, 99.1, 99.5, or about 99.9 percent sequence identity with a wild-type FkpA amino acid sequence.

As used herein, "signal sequence" or "signal polypeptide" refers to a peptide that can be used to secrete a heterologous polypeptide into the periplasm or medium of the cultured bacteria or to secrete proteins into the periplasm. A signal sequence is understood to direct post-translational transport of a protein. The signal sequence for a heterologous polypeptide may be homologous to the bacteria, or they may be heterologous, including signals native to the polypeptide being produced in the bacteria. Various signal peptides are known in the art, and these peptides are typically 3-60 amino acids long.

An "over-expressed" gene product is one that is expressed at levels greater than normal endogenous expression for that gene product. It can be accomplished, e.g., by introducing a recombinant construct that directs expression of a gene product in a host cell, or by altering basal levels of expression of an endogenous gene product, e.g., by inducing its transcription.

The promoters of this invention may be "inducible" promoters, i.e., promoters which direct transcription at an increased or decreased rate upon binding of a transcription factor. Alternatively, the promoters may be "constitutive," i.e., an unregulated promoter that allows for continual transcription of its associated gene.

"Transcription factors" as used herein include any factors that can bind to a regulatory or control region of a promoter and thereby effect transcription. The synthesis or the promoter binding ability of a transcription factor within the host cell can be controlled by exposing the host to an "inducer" or removing an inducer from the host cell medium. Accordingly, to regulate expression of an inducible promoter, an inducer is added or removed from the growth medium of the host cell. Various inducible promoters are known in that art and may be used with the present invention; these inducible promoters include chemically-regulated promoters (e.g., alcohol-regulated, tetracycline-regulated, steriod-regulated, metal-regulated, and pathogenesis-regulated promoters) and physically-regulated promoters (e.g., light-regulated promoters or temperature-regulated promoters, e.g., as described in U.S. Pat. No. 5,447,858).

As used herein, the phrase "induce expression" means to increase the amount of transcription of a specific gene by exposing a cell containing the gene to an effector or inducer, which results in increased transcription of the gene.

An "inducer" is a chemical or physical agent which, when given to a population of cells, will increase the amount of transcription from specific genes. These are usually small molecules whose effects are specific to particular operons or groups of genes, and can include sugars, phosphate, alcohol, metal ions, hormones, heat, cold, and the like. For example, isopropylthio-β-galactoside (IPTG) and lactose are inducers of the tac promoter, and L-arabinose is a suitable inducer of the arabinose promoter. The pho gene promoter, such as phoA and pho5, is inducible by low phosphate concentrations in the medium.

As used herein, "polypeptide" or "polypeptide of interest" refers generally to peptides and proteins having more than about ten amino acids, e.g., from 1-1000, 1-500, 1-400, 1-300, 1-200 amino acids or any number derivable therein. Preferably, the polypeptides are "exogenous" meaning that they are "heterologous", i.e., foreign to the host cell being utilized, such as a human protein produced by a CHO cell, or a yeast polypeptide produced by a mammalian cell, or a human polypeptide produced from a human cell line that is not the native source of the polypeptide.

Heterologous Polypeptides

Polypeptides of the present invention (e.g., a FkpA-Dsb polypeptide) may be used to allow for proper folding and disulfide bond formation of a heterologously expressed mammalian protein. It is anticipated that a practitioner may use the present invention with virtually any protein containing, e.g., two or more non-native disulfide bonds. Examples of mammalian polypeptides that may be expressed heterologously in a bacterial cell with a polypeptide of the present invention to generate a disulfide bond in the mammalian polypeptide include molecules such as, e.g., renin, a growth hormone (e.g., human growth hormone, bovine growth hormone, etc.), growth hormone releasing factor, growth factors, a hormone (e.g., parathyroid hormone, thyroid stimulating hormone), lipoproteins, a1-antitrypsin, insulin or an insulin chain (e.g., insulin A-chain, insulin β-chain), proinsulin, thrombopoietin, follicle stimulating hormone, calcitonin, luteinizing hormone, glucagon, a clotting factor (e.g., factor VIIIC, factor IX, tissue factor, von Willebrands factor), anti-clotting factors such as Protein C, an atrial naturietic factor, lung surfactants, a plasminogen activator such as human tPA or urokinase, mammalian trypsin inhibitor, brain-derived neurotrophic growth factor (BDNF), a kallikrein, CTNF, gp120, anti-HER-2, DNases, IGF-I, IGF-II, brain IGF-I, human chorionic gonadotropin, mammalian pancreatic trypsin inhibitors, an antibody fragment, protease inhibitors, therapeutic enzymes, lymphokines, cytokines, immunotoxins, bombesin, thrombin, tumor necrosis factor -α and -β, enkephalinase, a serum albumin (e.g., human serum albumin, bovine serum albumin, etc.), a mullerian-inhibiting substance, relaxin A-chain, relaxin B-chain, prorelaxin, mouse gonadotropin-associated peptide, a microbial protein (e.g., β-lactamase), inhibin, activin, vascular endothelial growth factor (VEGF), a receptor for a hormone or growth factors, integrin, protein A or D, a rheumatoid factor, a neurotrophic factors such as neurotrophin-3, -4, -5, or -6 (NT-3, NT-4, NT-5, or NT-6), or a nerve growth factor such as NGF-β, a cardiotrophin (cardiac hypertrophy factor) such as cardiotrophin-1 (CT-1), platelet-derived growth factor (PDGF), a fibroblast growth factor such as -α FGF and -β FGF, epidermal growth factor (EGF), a transforming growth factor (TGF), TGF-α, a TGF-β (e.g., TGF-β1, TGF-β2, TGF-β3, TGF-β4, or TGF-β5), insulin-like growth factor-I and -II (IGF-I and IGF-II), des(1-3)-IGF-I (brain IGF-I), an insulin-like growth factor binding protein, a CD protein (e.g., CD-3, CD-4, CD-8, CD-19), erythropoietin, osteoinductive factors, immunotoxins, bone morphogenetic proteins (BMPs), interferons such as interferon-α, -β, and -γ, colony stimulating factors (CSFs) (e.g., M-CSF, GM-CSF, G-CSF), interleukins (Ils) such as IL-1 to IL-10, anti-HER-2 antibody, superoxide dismutase, T-cell receptors, surface membrane proteins, decay accelerating factor, viral antigens such as a portion of the AIDS envelope, transport proteins, homing receptors, addressins, regulatory proteins, antibodies, antigens such as gp120(IIIb), and derivatives or active fragments of any of the peptides listed herein.

The polypeptides may be native or mutated polypeptides, and preferred sources for such mammalian polypeptides include human, bovine, equine, porcine, lupine, and rodent sources. In certain embodiments, human proteins are used.

In one embodiment, in addition to native tPA, the inventors contemplate the production of tPA variants and derivatives using the disclosed methods and compositions. Examples of tPA variants contemplated to be useful in the practice of the present invention include:

(1) tPA variants which have an extra glycosylation site at amino acid positions 103-105, the native glycosylation site removed at position 117, and at least one amino acid substituted in the 296-299 amino acid region of native human tPA. A specific molecule within this group is T103N, N117Q, KHRR (9296-299)AAAA tPA (TNK tPA), where the amino acids replaced are indicated to the left and the amino acids substituted for them to the right of the amino acid position(s) shown. These molecules, which have an extended half-life and improved fibrin specificity as compared to wild-type human tPA, and show substantial resistance to the fast acting plasminogen activator inhibitor (PAI-1), are specifically disclosed, for example, in Intl. Pat. Appl. Publ. No. WO/93/24635.

(2) N-terminally truncated tPA variants, and specifically the plasminogen activator K2P (BM 06.002) described, for example, in Eur. Pat. Appl. No. EP 0382174. These variants contain the kringle 2 (K2) and protease (P) domains of human tPA, and due to its expression in *E. coli* is present in an unglycosylated form. K2P has been described to have a reduced clearance and a longer plasma half-life. Other tPA variants which may be used with the present invention include those described in Eur. Pat. Appl. No. EP 196920; Eur. Pat. Appl. No. EP 207589; Aust. Pat. Appl. No. AU 61804/86; Eur. Pat. Appl. No. EP 231624; Eur. Pat. Appl. No. EP 289508; Eur. Pat. Appl. No. EP 234051; Eur. Pat. Appl. No. EP 263172; Eur. Pat. Appl. No. EP 24208; Eur. Pat. Appl. No. EP 292009; Eur. Pat. Appl. No. EP 297066; Eur. Pat. Appl. No. EP 302456; Eur. Pat. Appl. No. EP 379890; Joly et al., (1997).

(3) Vampire bat tPAs (BatPAs), as disclosed, e.g., in Eur. Pat. Appl. No. EP 352119; and (4) A tPA variant having cysteine at position 84 of native tPA replaced by serine (C84S tPA), described, e.g., in Suzuki et al. (1993).

DNA Expression

The expression "control sequences" refers to DNA sequences necessary for the expression of an operably linked coding sequence in a particular host organism. The control sequences that are suitable for bacteria include the alkaline phosphatase promoter, optionally an operator sequence, and a ribosome-binding site.

A nucleic acid is "operably" or "operatively" linked when it is placed into a functional relationship with another nucleic acid sequence. For example, DNA for a presequence or secretory leader is operably/operatively linked to DNA for a polypeptide if it is expressed as a preprotein that participates in the secretion of the polypeptide; a promoter or enhancer is operably/operatively linked to a coding sequence if it affects the transcription of the sequence; or a ribosome binding site is operably linked to a coding sequence if it is positioned so as to facilitate translation. Linking can be accomplished by ligation at convenient restriction sites. If such sites do not exist, synthetic oligonucleotide adaptors or linkers may be used in accordance with conventional practice.

Cell Lines

As used herein, the expressions "cell", "cell line", and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

DsbC and DsbG

DsbC is a soluble periplasmic oxidoreductase which is thought to act in parallel with DsbA (Missiakas et al., 1994; Bardwell et al., 1993; Bardwell, 1994). Unlike DsbA which exhibits low disulfide isomerase activity in vitro, DsbC has been shown to be an efficient catalyst of disulfide bond isomerization (Zapun et al., 1995).

DsbG is a soluble periplasmic oxidoreductase which has properties similar to DsbC. Unlike DsbA which exhibits low disulfide isomerase activity in vitro, DsbG is an efficient catalyst of disulfide bond isomerization (U.S. Pat. No. 6,083, 715).

Methods of Nucleic Acid Delivery and DNA Transformation

In certain embodiments, the present invention provides recombinant host cells transformed with polynucleotides which encode novel hybrid disulfide bond isomerases and particular disulfide bond-containing polypeptides of interest, as well as transgenic cells derived from those transformed or transfected cells. In particular embodiments, a recombinant host cell of the present invention is transformed with a polynucleotide comprising a sequence encoding a hybrid FkpA-DsbA polypeptide and a polynucleotide comprising a sequence encoding a heterologous polypeptide that contains disulfide bonds, for instance tissue plasminogen activator (tPA) or a variant of tPA. Means of transforming cells with exogenous polynucleotides such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook et al., 1989).

For example, electroporation can be used to transform cells such as bacterial cells. The application of brief, high-voltage electric pulses to a cell culture can lead to the formation of nanometer-sized pores in the cell membrane. DNA is taken directly into the cytoplasm either through these pores or as a consequence of the redistribution of membrane components that accompanies closure of the pores. Electroporation can be extremely efficient and can be used both for transient expression of cloned genes and for establishment of cell lines that carry integrated copies of a gene of interest. Electroporation, in contrast to calcium chloride-mediated transformation, frequently gives rise to high numbers of target cells being transformed with the foreign DNA.

Liposome and Nanocapsule Transformation

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

In certain embodiments, the inventors contemplate the use of liposomes and/or nanocapsules for the introduction of particular peptides or nucleic acid segments into host cells. Such formulations may be preferred for the introduction of nucleic acids, peptides, and/or antibodies derived therefrom. The formation and use of liposomes is generally known to those of skill in the art (see, e.g., Couvreur et al., 1977 and Gabizon and Papahadjopoulos, 1988).

Recombinant Expression of Heterologous Proteins in Bacteria

The present inventors contemplate expression of polypeptides in conjunction with a disulfide bond isomerase of the present invention. A technique often employed by those skilled in the art of protein production is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule. Techniques such as these would also, of course, be appropriate for the production of a disulfide bond-containing polypeptide in accordance with the present invention.

The first step in such cloning procedures is the screening of an appropriate DNA library, such as a rat, human, bovine, or other mammalian-derived library. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature, for example, in Sambrook et al. (1989). Moreover, as the present invention encompasses the cloning of genomic segments as well as cDNA molecules, it is contemplated that other suitable methods known to those in the art, such as, e.g., those described by Spoerel et al. (1987), may also be used in connection with cloning a disulfide bond-containing polypeptide, or alternatively to express a hybrid polypeptide, such as a hybrid FkpA-DsbA polypeptide (e.g., that displays disulfide bond isomerase, and/or chaperone activity in vivo or in vitro and directs the folding and isomerization of disulfide bonds contained within a disulfide bond-containing polypeptides of interest).

After identifying appropriate DNA molecules, they may be inserted into any one of the many vectors currently known in the art and transferred to a host cell where it will direct the expression and production of the so-called recombinant version of the protein. This is also, of course, routinely practiced in the art and described in various publications, such as, e.g., Sambrook et al. (1989). Such DNA segments may be contained on a single plasmid vector, or alternatively, the isomerase/chaperone may be encoded by a nucleic acid sequence on one vector and the disulfide bond-containing polypeptide of interest may be present on a second plasmid vector which is compatible for co-residence in a single host cell with the first plasmid vector comprising the isomerase/chaperone sequence. The selection of plasmid vectors is well-known to those of skill in the art, and such a selection may be based on the incompatibility grouping of such vectors (IncP, IncQ, etc.). Virtually any such plasmid vectors may be used in the practice of the invention. In one embodiment, preferred replicons include pACYC184 and pTI103.

It will be understood that recombinant disulfide bond-containing polypeptides may differ from naturally-produced polypeptides in certain ways. In particular, the degree of post-translational modifications, such as, for example, glycosylation and phosphorylation may be different between the recombinant and natural forms.

Recombinant clones expressing nucleic acid segments which encode eukaryotic disulfide-bond containing polypeptides may be used to prepare purified recombinant polypeptides, purified polypeptide-derived antigens as well as mutant or variant recombinant protein species in significant quantities. In particular, the invention provides for the production of recombinant polypeptides in substantial quantities from bacterial host cells.

Additionally, by application of techniques such as DNA mutagenesis, the present invention allows the ready preparation of so-called "second generation" molecules having modified or simplified protein structures. Second generation proteins will typically share one or more properties in common with the full-length polypeptides, such as a particular antigenic/immunogenic epitopic core sequences, or particular catalytic sites, active sites, or ligand binding domains, etc. Epitopic sequences can be provided on relatively short molecules prepared from knowledge of the peptide or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence. This is particularly desirable in the preparation of recombinant polypeptides having enhanced or superior stability, activity, binding, or affinity for substrates and the like.

The general process of recombinant expression of proteins in bacterial hosts, and particularly Gram-negative hosts, is well-known to those of skill in the art. It is generally beneficial for the methods described herein that the DNA sequence encoding the particular eukaryotic protein of interest to be secreted be operatively linked to a DNA sequence which encodes a signal peptide sufficient for the translocation of the recombinant polypeptide to the periplasmic space of the bacterial host cell. As is well-known, operative links between such DNA sequences mean that a translational fusion exists between the heterologous protein and the signal peptide. As a rule, such signal peptides form the N-terminal portion of the secreted heterologous protein. Signal sequences which promote protein translocation to the periplasmic space of Gram-negative bacterial are well-known, as exemplified by those described herein. The E. coli OmpA, Lpp, LamB, MalE, PelB, and StII leader peptide sequences have been successfully used in many applications as signal sequences to promote protein secretion in bacterial cells such as those used herein, and are all contemplated to be useful in the practice of the invention.

Promoters, Enhancers, and Signal Sequence Elements

Promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

Examples of useful promoters include the lac-lpp promoter which is well-known in the art. Other non-limiting examples of promoters contemplated to be useful in the practice of the invention include the ara, tet, tac, trc, trp, phoA, $P_{BAD}$, $\lambda_{PL}$, lpp, and T7 promoters.

Site-Specific Mutagenesis

Site-specific mutagenesis is a technique useful in the preparation of individual peptides, or biologically functional equivalent proteins or peptides, through specific mutagenesis of the underlying DNA. The technique, well-known to those of skill in the art, further provides the ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 1 to about 10 residues on both sides of the junction of the sequence being altered.

In general, the technique of site-specific mutagenesis is well known in the art, as exemplified by various publications. As will be appreciated, the technique typically employs a phage vector which exists in both a single-stranded and double-stranded form. Typical vectors useful in site-directed mutagenesis include vectors such as the M13 phage. These phage are readily commercially-available and their use is generally well-known to those skilled in the art. Double-stranded plasmids are also routinely employed.

PCR-based strand overlap extension (SOE) for cloning and site-directed mutagenesis was utilized for preparing the nucleic acid compositions of the present invention. The techniques of PCR are well-known to those of skill in the art (e.g., U.S. Pat. Nos. 4,683,195; 5,023,171). The SOE procedure involves a two-step PCR protocol, in which a complementary pair of internal primers (B and C) are used to introduce the appropriate nucleotide changes into the wild-type sequence. In two separate reactions, flanking PCR primer A (restriction site incorporated into the oligo) and primer D (restriction site incorporated into the oligo) are used in conjunction with primers B and C, respectively to generate PCR products AB and CD. The PCR products are purified by agarose gel electrophoresis and the two overlapping PCR fragments AB and CD are combined with flanking primers A and D and used in a second PCR reaction. The amplified PCR product is agarose gel purified, digested with the appropriate enzymes, ligated into an expression vector, and may be transformed into E. coli JM101, XL1-Blue™ (Stratagene, La Jolla, Calif.), JM105, TG1 (Carter et al., 1985), or other such suitable cells as deemed appropriate depending upon the particular application of the invention. Clones are isolated and the mutations can be confirmed by sequencing of the isolated plasmids.

Beginning with the native gene sequences (for example, the nucleic acid sequences encoding a eukaryotic disulfide-bond-containing polypeptide such as tPA or the like), suitable clones and subclones may be made in the appropriate vectors from which site-specific mutagenesis may be performed.

Biological Functional Equivalents

Modification and changes may be made in the structure of a peptide of the present invention, and/or the DNA segment which encodes it, and result in a functional molecule that encodes a protein or peptide with desirable characteristics. For example, FkpA and DsbA could be altered in accordance with the invention (e.g., via a substitution or deletion mutation, etc.). The following is a discussion based upon changing the amino acids of a protein to create an equivalent, or even an improved, second-generation molecule.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, ie. still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within +−0.1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

MODES FOR CARRYING OUT THE INVENTION

In one embodiment of the invention, expression of a hybrid disulfide bond isomerase gene may be induced prior to heterologous gene expression. The heterologous polypeptide and the FkpA-DsbA hybrid (chimera) polypeptide may be secreted into the periplasm, or the heterologous polypeptide may be secreted into the culture medium of the bacteria which may also contain a nucleic acid encoding the polypeptide. In certain embodiments, the polypeptide is recovered from the periplasm of the bacteria.

The fkpA and dsbA genes used to create the FkpA-DsbA chimera may be derived from any bacterial source, e.g., from E. coli. A gene encoding the chimera polypeptide may be separately placed from a gene encoding a heterologous polypeptide if the nucleic acids are on the same vector. In addition, the nucleic acid encoding the FkpA-DsbA hybrid and the nucleic acid encoding the heterologous polypeptide will often be under separate, different inducible promoters so that induction of expression can occur in the required sequential order. The nucleic acid encoding the FkpA-DsbA chimera and the nucleic acid encoding the heterologous polypeptide may be integrated into the host cell genome or contained on autonomously replicating plasmids.

In one embodiment, the bacteria comprises two separate vectors respectively containing the nucleic acid encoding the engineered FkpA-DsbA chimera polypeptide and the nucleic acid encoding the heterologous polypeptide.

In another embodiment, the nucleic acid encoding the FkpA-DsbA chimera polypeptide and the nucleic acid encoding the heterologous polypeptide are contained on the same vector but are under the control of separate inducible promoters and separate signal sequences.

In a third embodiment, the nucleic acid encoding the FkpA-DsbA chimera polypeptide and the nucleic acid encoding the heterologous polypeptide are contained on the same vector and are under the control of a single promoter.

In a fourth embodiment the FkpA and DsbA domains of the disulfide isomerase are encoded by different vectors. Each of the FkpA and DsbA proteins are expressed as fusions to dimerizing domains such as those derived from well known heterodimeric leucine zipper (e.g., from the transcriptiona activator SCN4). The FkpA and DsbA fusions to the respective halves of the leucine zipper associate in the bacterial periplasm to form a protein, comprising of four polypeptides: two FkpA chains that associate with two DsbA chains via leucine zipper interactions.

The heterologous nucleic acid (e.g., cDNA or genomic DNA) can be suitably inserted into a replicable vector for expression in the bacterium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes, and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli may be transformed using pBR322, a plasmid derived from an E. coli species (see, e.g., Bolivar et al., 1977). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide may also contain an inducible promoter that is recognized by the host bacterial organism and is operably linked to the nucleic acid encoding the polypeptide of interest. It may also contain a separate inducible promoter operably linked to the nucleic acid encoding the FkpA-DsbA chimera. Inducible promoters suitable for use with bacterial hosts include the β-lactamase and lactose (lac) promoter systems (Chang et al., 1978; Goeddel et al., 1979), the arabinose (ara) promoter system (Guzman et al., 1995), alkaline phosphatase (phoA), a tryptophan (trp) promoter system (Goeddel, 1980; Eur. Pat. Appl. Publ. No. EP 36,776), $\lambda_{PL}$ promoter, and hybrid promoters such as the tac promoter. However, other known bacterial inducible promoters are suitable. Their nucleotide sequences have been published, thereby enabling a skilled worker to operably ligate them to DNA encoding the polypeptide of interest or to the fkpA-dsbA hybrid gene (Siebenlist et al., 1980) using linkers or adaptors or other methods to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA. Construction of suitable vectors containing one or more of the above-listed components employs standard ligation techniques. Isolated plasmids or DNA fragments are cleaved, tailored, and re-ligated in the form desired to generate the plasmids required.

Suitable bacteria for this purpose include Archaebacteria and Eubacteria, especially Eubacteria, and most preferably Enterobacteriaceae. Examples of useful bacteria include Escherichia, Enterobacter, Azotobacter, Erwinia, Bacillus, Pseudomonas, Klebsiella, Proteus, Salmonella, Serratia, Shigella, Rhizobia, and Paracoccus. Suitable E. coli hosts include E. coli SF110, E. coli 294 (ATCC 31446), E. coli B, and E. coli $_\chi$1776 (ATCC 31537). These examples are illustrative rather than limiting. Mutant cells of any of the above-mentioned bacteria may also be employed, including ones that display an altered redox potential in their periplasm and/or cytoplasm. It is, of course, necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon.

Host cells can be transfected and preferably transformed with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation can be done using standard techniques appropriate to such cells. The calcium treatment employing calcium chloride, as described in section 1.82 of Sambrook et al., (1989), is generally used for bacterial cells that contain substantial cell-wall barriers. Another method for transformation employs polyethylene glycol/DMSO. Yet another method is the use of the technique termed electroporation.

Bacterial cells used to produce the polypeptide of interest for purposes of this invention can be cultured in suitable media in which the promoters for the nucleic acid encoding the heterologous polypeptide and for the nucleic acid encoding DsbC can be artificially induced as described generally, e.g., in Sambrook et al. (1989). Examples of suitable media are given in U.S. Pat. Nos. 5,304,472 and 5,342,763.

Any necessary supplements besides carbon, nitrogen, and inorganic phosphate sources may also be included at appropriate concentrations introduced alone or as a mixture with another supplement or medium such as a complex nitrogen source. The pH of the medium may be any pH from about 5-9, depending mainly on the host organism. Preferably, the medium contains no reduced glutathione, and the bacteria are not cultured so as to over-express nucleic acid encoding the heat-shock transcription factor, RpoH.

Gene expression may be measured in a sample directly, for example, by conventional northern blotting to quantitate the transcription of mRNA (Thomas, 1980). Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively gene expression may be measured based on the activity of the protein that is being produced.

Procedures for observing whether an expressed or over-expressed gene product is secreted are readily available to the skilled practitioner. Once the culture medium is separated from the host cells, for example, by centrifugation or filtration, the gene product can then be detected in the cell-free culture medium by taking advantage of known properties characteristic of the gene product. Such properties can include the distinct immunological, enzymatic, or physical properties of the gene product.

For example, if an over-expressed gene product has a unique enzyme activity, an assay for that activity can be performed on the culture medium used by the host cells. Moreover, when antibodies reactive against a given gene product are available, such antibodies can be used to detect the gene product in any known immunological assay (e.g., as in Harlow and Lane, 1988).

The secreted gene product can also be detected using tests that distinguish polypeptides on the basis of characteristic physical properties such as molecular weight. To detect the physical properties of the gene product, all polypeptides newly synthesized by the host cell can be labeled, e.g., with a radioisotope. Common radioisotopes that can be used to label polypeptides synthesized within a host cell include tritium ($^{3}H$), carbon-14 ($^{14}C$), sulfur-35 ($^{35}S$), and the like. For example, the host cell can be grown in $^{35}S$-methionine or $^{35}S$-cysteine medium, and a significant amount of the $^{35}S$ label will be preferentially incorporated into any newly synthesized polypeptide, including the over-expressed heterologous polypeptide. The $^{35}S$-containing culture medium is then removed and the cells are washed and placed in fresh non-radioactive culture medium. After the cells are maintained in the fresh medium for a time and under conditions sufficient to allow secretion of the $^{35}S$-radiolabeled expressed heterologous polypeptide, the culture medium is collected and separated from the host cells. The molecular weight of the secreted, labeled polypeptide in the culture medium can then be determined by known procedures, e.g., polyacrylamide gel electrophoresis. Such procedures, and/or other procedures for detecting secreted gene products, are provided in Goeddel (1990), and Sambrook et al, (1989).

For secretion of an expressed or over-expressed gene product, the host cell is cultured under conditions sufficient for secretion of the gene product. Such conditions include, e.g., temperature, nutrient, and cell density conditions that permit secretion by the cell. Moreover, such conditions are those under which the cell can perform basic cellular functions of transcription, translation, and passage of proteins from one cellular compartment to another, as are known to those skilled in the art.

In practicing the process of this invention, the yield of biologically active polypeptide is generally increased, while yield of insoluble polypeptide is not changed or is decreased, i.e., yield of soluble and biologically active polypeptide is increased.

The polypeptide of interest may be recovered from the periplasm or culture medium as a secreted soluble polypeptide. It may be useful to purify the polypeptide of interest from recombinant cell proteins or polypeptides and from the FkpA-DsbA hybrid protein to obtain preparations that are substantially homogeneous as to the polypeptide of interest. As a first step, the culture medium or lysate may be centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane associated or, more preferably, completely soluble in the periplasm or culture supernatant. The polypeptide thereafter may be further solubilized and/or refolded, if necessary, and purified from contaminant soluble proteins and polypeptides.

Alternatively, expression of FkpA-DsbC without a signal sequence may be employed in conjunction with strains that have an oxidizing cytoplasm, such as the Origami™ E. coli strains marketed by Novagen/EMD Biosciences (Madison, Wis.). In this strain background, protein disulfides are formed in cytoplasmic proteins and the artificial disulfide isomerase proteins disclosed herein allow an increase in the yield of the correctly folded and biologically active polypeptide.

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 de novo Design of Disulfide Isomerase

A study was undertaken for the de novo design of a protein able to assist the folding of multi disulfide containing proteins when overexpressed in the periplasm of *E. coli*. Engineered to contain no amino acid homology with the main bacterial protein disulfide isomerase DsbC, the rational design of this enzyme sought to recapitulate the essential features for bacterial disulfide isomerization. Previously, in fact, a number of complementary strategies for elucidating the molecular features of DsbC function have been investigated. In particular, it was hypothesized that the molecular requirements for a protein that can catalyze isomerization of non-native disulfides in vivo are: (i) the presence of a peptide binding cleft with chaperone activity, and (ii) the presence of two catalytic domains with a thioredoxin fold. In addition, the overall molecular topology of disulfide isomerases must depend on (iii) the relative orientation of the active sites, which is in turn influenced by the nature of the α-helical linker connecting the thioredoxin domain to the rest of molecule (Segatori et al., 2004).

Artificial enzymes were designed to resemble the gross topology of DsbC, i.e., a V-shaped homodimeric molecule that contains a region for the binding with the substrate between the arms of the V. FkpA is a homodimeric V-shaped protein with cis/trans peptidyl-prolyl isomerase activity in which each monomer is formed by an N-terminal dimerization domain and a C-terminal catalytic domain, joined by a long α-helical linker. The two structural domains have been demonstrated to be stable on their own, and to function independently (Saul et al., 2004). In particular, the dimerization domain exhibits chaperone activity and it has been reported to form a binding pocket for the interaction with the substrate (Ramm and Pluckthun, 2001). A series of artificial enzymes were constructed, comprising the minimal FkpA N-terminal domain that has been shown to exhibit chaperone activity which includes a long α-helical liker at the C-terminus (Saul et al., 2004), fused to the DsbA molecule (FIG. 1).

Example 2

Construction of FkpA-DsbC Chimera Proteins

Bacterial strains and plasmids used in this study are listed in Table 1. The genes encoding FkpA-DsbA chimeric proteins were constructed by overlap extension PCR (e.g., Aiyar et al., 1996; U.S. Pat. No. 5,023,171) using the primers listed in Table 2 (SEQ ID NOs:16-45), digested with XbaI and HindIII and cloned into pBAD33 (Guzman, et al., 1995). All the chimeras contained a C-terminal hexahistidine tag. For protein purification purposes the gene fusions were digested with XbaI and HindIII, ligated into pET28a (Novagen, Madison Wis.) and transformed into *E. coli* BL21(DE3) cells.

TABLE 1

| | Relevant Genotype | Source |
|---|---|---|
| Strains | | |
| DH5a | F-(f80dlacZ-MI5)-(lac/ZY A-argF) U 169 deoR recA I endAl hsdR17(rk–, mk+)supE44, thi-1 gyrA96, re/Al | Laboratory Collection |
| DH B4 | araD139 (araA–/eu)7679 (codB–/ac)X74 ga/E15 ga/K16 rpsL150 re/Al thi phoA (Pvull) phoR ma/F3 F [lac+ (lad) pro] | Laboratory Collection |
| MC1000 | araD139 (araA–/eu) 7679 (cod8–lac)X74 01E15 ga/Kl 6 rpsL 150 re/Al thi F [lac+ (lac/) pro] | Casadaban, 1980 |
| LM106 | MC1000 dsbA::kan5 | Laboratory Collection |
| LM102 | MC1000 dsbB::kan5 | Masip, 2004 |
| PB351 | SFI0ODdegP::kan DsbC | Bessette, 2001 |
| PB401 | SFI0ODdegP::kan DsbA | Bessette, 2001 |
| BL21(DE3) | F ompT dcm (DE3) | Laboratory Collection |
| M B706 | DHB4 DsbC, dsbA::kan | Beckwith laboratory |
| Plasmid | | |
| pET-28(a) | T7 expression vector, C-terminal 6× histidine tag | Novagen |
| pBADdsbC | dsbC from *Escherichia coil* in pBAD33 | Laboratory Collection |
| pBADdsbA | dsbA from *Escherichia coil* in pBAD34 | Laboratory Collection |
| pTrcStl IvtPA | tPA(46-175) with Stll leader in pTrc99A | Joly, 1997 |
| pBAD-FkpADsbA1 | FkpA(1-114) fused to DsbA(1-189) in pBAD33 | This work |
| pBAD-FkpADsbA2 | FkpA(1-114) fused to DsbA(2-189) in pBAD33 | This work |
| pBAD-FkpADsbA3 | FkpA(1-114) fused to DsbA(3-189) in pBAD33 | This work |
| pBAD-FkpADsbA4 | FkpA(1-114) fused to DsbA(4-189) in pBAD33 | This work |
| pBAD-FkpADsbA5 | FkpA(1-114) fused to DsbA(5-189) in pBAD33 | This work |
| pET28-FkpADsbA2 | FkpA(1-114) fused to DsbA(2-189) in pET28 | This work |
| pET28-FkpADsbA3 | FkpA(1-114) fused to DsbA(3-189) in pET28 | This work |
| pET28-FkpADsbA4 | FkpA(1-114) fused to DsbA(4-189) in pET28 | This work |
| pET28-FkpADsbA5 | FkpA(1-114) fused to DsbA(5-189) in pET28 | This work |

TABLE 2

Primers used (SEQ ID NOs: 16-45)

| | | SEQ ID |
|---|---|---|
| XbaIDsbCss.f | GAGCTCGAATTCTCTAGATTAAAGAGGAGAAAGGTACCCATGATGAAGAAAGGTTTTAT | 16 |
| 1.f | ATGAAGAAAGGTTTTATGTTGTTTACTT | 17 |
| 2.r | AAGCCTGAAAACGCCGCTAACAAAGTAAACAACATAAAACCTT | 18 |
| 3.f | GTTAGCGGCGTTTTCAGGCTTTGCTCAGGCTGCTGAAGCTGCA | 19 |
| 4.r | TGTCAGCAGCTGTAGCAGGTTTTGCAGCTTCAGCAGCCTGAGC | 20 |
| 5.f | AACCTGCTACAGCTGCTGACAGCAAAGCAGCGTTCAAAAATGA | 21 |
| 6.r | TGCATAAGCTGATTTCTGATCGTCATTTTTGAACGCTGCTTTG | 22 |
| 7.f | GATCAGAAATCAGCTTATGCACTGGGTGCCTCGCTGGGTCGTT | 23 |
| 8.r | TCTTTTAGAGAGTTTTCCATGTAACGACCCAGCGAGGCACCCA | 24 |
| 9.f | CATGGAAAACTCTCTAAAAGAACAAGAAAAACTGGGCATCAAA | 25 |
| 10.f | CGATCAGCTGATCTTTATCCAGTTTGATGCCCAGTTTTTCTTG | 26 |
| 11.f | TGGATAAAGATCAGCTGATCGCTGGTGTTCAGGATGCATTTGC | 27 |
| 12.r | GTCGGAGAGTTTGCTCTTATCAGCAAATGCATCCTGAACACCA | 28 |
| 13.f | GATAAGAGCAAACTCTCCGACCAAGAGATCGAACAGACTCTAC | 29 |
| 14.r | TTCACGCGAGCTTCGAATGCTTGTAGAGTCTGTTCGATCTCTT | 30 |
| 15.f | AGCATTCGAAGCTCGCGTGAAGTCTTCTGCTCAGGCGAAGATG | 31 |
| 16.r | CGTTATCAGCCGCGTCTTTTTCCATCTTCGCCTGAGCAGAAGA | 32 |
| 17.f | AAAAAGACGCGGCTGATAACGAAGCAAAAGGTAAAGAGTACCG | 33 |
| 18.r | TTTCTCTTTGGCAAATTTCTCGCGGTACTCTTTACCTTTTGCT | 34 |
| fkpA 11-dsbA1.r | CTGTTTACCATCTTCATACTGCGCTTTCTCTTTGGCAAATTTC | 35 |
| fkpA 11-dsbA2.r | GTAGTGTACTGTTTACCATCTTCATACTGTTTCTCTTTGGCAAATTTC | 36 |
| fkpA 11-dsbA3.r | CAGGGTAGTGTACTGTTTACCATCTTCATATTTCTCTTTGGCAAATTTC | 37 |
| fkpA 11-dsbA4.r | CAGGGTAGTGTACTGTTTACCATCTTCTTTCTCTTTGGCAAATTTC | 38 |
| fkpA 11-dsbA5.r | CAGGGTAGTGTACTGTTTACCATCTTTCTCTTTGGCAAATTTC | 39 |
| fkpAdsbA1.f | GAAATTTGCCAAAGAGAAAGCGCAGTATGAAGATGGTAAACAG | 40 |
| fkpAdsbA2.f | GAAATTTGCCAAAGAGAAACAGTATGAAGATGGTAAACAGTACACTAC | 41 |
| fkpAdsbA3.f | GAAATTTGCCAAAGAGAAATATGAAGATGGTAAACAGTACACTACCCTG | 42 |
| fkpAdsbA4.f | GAAATTTGCCAAAGAGAAAGAAGATGGTAAACAGTACACTACCCTG | 43 |
| fkpAdsbA5.f | GAAATTTGCCAAAGAGAAAGATGGTAAACAGTACACTACCCTG | 44 |
| DsbAHisHindIII.r | TTTTTAAGCTTTTAGTGGTGGTGGTGGTGGTGTTTTTTCTCGGACAGATATTTC | 45 |

The FkpA polypeptide is a homodimeric V-shaped molecule with overall structural architecture (gross topology) similar to DsbC. Each monomer is composed of an N-terminal dimerization domain (residues 1-114; FIG. 1; SEQ ID NO:2) and a C-terminal catalytic domain (residues 115-224) (FIG. 1). Residues 70-114 form a long α-helical linker that joins the two independent domains in each monomer. A series of fusions were constructed, encoding the dimerization domain, specifically residues 1-114 (SEQ ID NO:2) of FkpA fused to the $1^{st}$, $2^{nd}$, $3^{rd}$, $4^{th}$, or $5^{th}$ residue of mature DsbA (SEQ ID NO:3), termed DsbA(1-189); DsbA(2-189), DsbA (3-189), DsbA(4-189), and DsbA(5-189), along with a hexahistidine tag, respectively, generating the respective molecules FkpA-DsbA1 (SEQ ID NO:4), FkpA-DsbA2 (SEQ ID NO:5), FkpA-DsbA3 (SEQ ID NO:6), FkpA-DsbA4 (SEQ ID NO:7), and FkpA-DsbA5 (SEQ ID NO:8). Differences in the nature of the amino acid region joining the two structurally independent domains are presumed to result in different orientations of the portion of the chimera protein at the C-terminal of the helical linker, i.e., the catalytic active sites. Furthermore, it has been reported that the relative orientation of the active sites in the thioredoxin domains is crucial to the catalytic function of the molecule (Segatori et al., 2004). The fkpA-dsbA gene fusions were placed downstream from the arabinose promoter in the medium copy number plasmid pBAD33 (Guzman et al. 1995). Following induction of protein expression with arabinose, the wild-type DsbC and all the FkpA-DsbA chimeras accumulated to nearly identical levels, as determined by Western blotting with a polyclonal antibody that recognizes the C-terminal His tag.

Example 3

In vivo Disulfide Bond Formation and Isomerization

To determine the effect of the FkpA-DsbA chimera constructs on the folding yield of a truncated version of the human tissue plasminogen containing 9 disulfide bonds, (vtPA, comprising the catalytic and kringle 2 domains of the full length protein), E. coli DHB4 (araD139 (araA-leu)7679 (codB-lac)X74 galE15 galK16 rpsL150 relA1 thi phoA (PvuII) phoR malF3 F'[lac⁺(lacI) pro]) and E. coli PB401 (SF100 ΔdegP::kan, dsbA::kan) were co-transformed with pBAD33 derivatives encoding the chimera genes, and with pTrcStIIvtPA, a pTrc99 derivative encoding the vtPA gene fused to the stII leader peptide (Bessette et al., 1999). Cultures were grown at 30° C. in 15 ml of LB medium with 50 μg/ml of ampicillin and 25 μg/ml of chloramphenicol. Cells were diluted 1:100 from overnight cultures, grown to $OD_{600}$ of 0.8, and arabinose was added to a final concentration of 0.2%; 30 min later, vtPA synthesis was induced with 1 mM isopropyl-β-D-thiogalactopyranoside (IPTG). Following growth for three additional hours, 6 ml aliquots were pelleted by centrifugation and stored at −20° C. The pellets were resuspended in cold PBS as needed to normalize the number of cells per sample, and lysed with a French press. Insoluble material was removed by centrifugation (12,000×g, 10 min at 4° C.), and the soluble protein concentration was determined by the Bio-Rad protein assay. tPA activities were obtained by first diluting the samples in 50 mM Tris-HCl (pH 7.4) with 0.01% Tween 80 to a final protein concentration of 0.5 μg/μl. 30 μl of the diluted cell lysates were added to 250 μl of the same buffer containing 0.04 μg/μl of human Glu-type plasminogen (American Diagnostica, Greenwich, Conn.), and 0.4 mM Spectrozyme PL (American Diagnostica), incubated at 37° C., and the change in $A_{405}$ was monitored. To study the in vivo oxidase activity of the chimeric proteins, E. coli LM106 (MC1000 dsbA::kan5) and LM102 (MC1000 dsbB::kan5) were transformed with the appropriate pBAD33 plasmid derivatives. Overnight cultures were grown in LB medium with 50 μg/ml of kanamycin and 25 μg/ml of chloramphenicol, and diluted 1:100 in low phosphate minimal medium containing MOPS salts, 0.2% glycerol, 0.2% glucose, 0.2% casein amino acids, and 0.5 μg/ml thiamine, with 50 μg/ml of kanamycin and 25 μg/ml of chloramphenicol. When the cell density reached $OD_{600}$=0.4, arabinose was added to a final concentration of 0.2% w/v. Four hours later, cells were collected and mixed with 0.4 M iodoacetamide and lysis buffer (B-PER™, Pierce) in a 1:2 ratio. The activity of alkaline phosphatase was determined as described previously (Brickmann and Beckwith, 1975).

To determine the ability of the FkpA-DsbA chimera to complement the activity of DsbC and DsbA in medium supplemented with $CuCl_2$, E. coli MB706 (araD139 (araA-leu)7679 (codB-lac)X74 galE15 galK16 rpsL150 relA1 thi phoA (PvuII) phoR malF3 F'[lac⁺(lacI) pro] ΔdsbC, dsbA::kan) was transformed with pBAD33 derivatives encoding the chimera genes and plated on brain and heart infusion (BHI) medium (1.5% agar). Cultures were grown at 37° C. in BHI medium supplemented with 50 μg/ml of ampicillin, 25 μg/ml of chloramphenicol, and 50 μg/ml of kanamycin. Cells were diluted 1:100 from O/N cultures in BHI medium, grown for two hours under the same conditions, and the $OD_{600}$ was measured. 100 μl of each culture, appropriately diluted to normalize the number of cells per sample (to $OD_{600}$=5*10⁵ cfu), were plated on BHI medium 1.5% agar, 0.2% arabinose, and supplemented with different $CuCl_2$ concentration, ranging from 0 to 12 mM, and antibiotics as described above. Plates were incubated at 37° C. for 18-22 hours.

Figure 2:
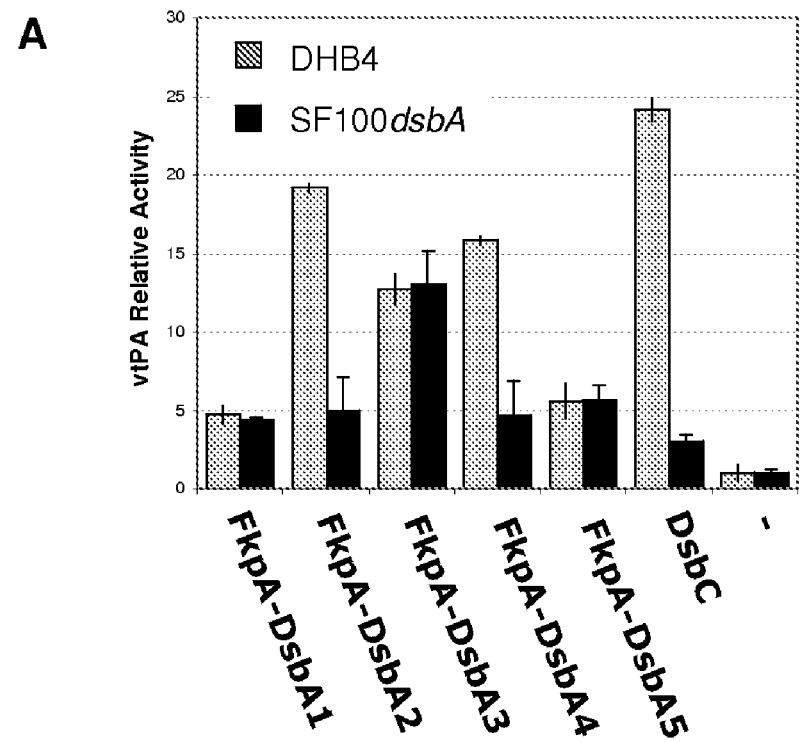
FIG. 2. Disulfide-bond formation in vivo. (A) Yield of active vtPA in dsbC or dsbA cells and relative expression levels of the FkpA-DsbA hybrid polypeptide. PB351 (SF100 ΔdsbC), or PB401 (SF100 dsbA) transformed with pTrcStI-IvtPA and pBAD derivatives encoding the respective fusion proteins were grown in LB media. Protein synthesis was induced as described in the Examples, and the yield of active vtPA at 3 h after induction was determined. Relative activities were obtained by dividing the $\Delta A_{405}$ (absorbance of each strain subtracted of the background consisting of a strain not expressing tPA) by the $\Delta A_{405}$ of a strain expressing vtPA alone. (B) PhoA activity. Effect of the expression of the chimeric proteins on alkaline phosphatase activity in the periplasm of MC1000 dsbA (white bars) and MC1000 dsbB (black bar). The alkaline phosphatase activity of the parental isogenic strain MC1000 is shown by the gray bar. Cells were induced with 0.2% arabinose, harvested in mid-log phase, and lysed, and activity assays were conducted as described in Examples 2-4.
Figure 2:
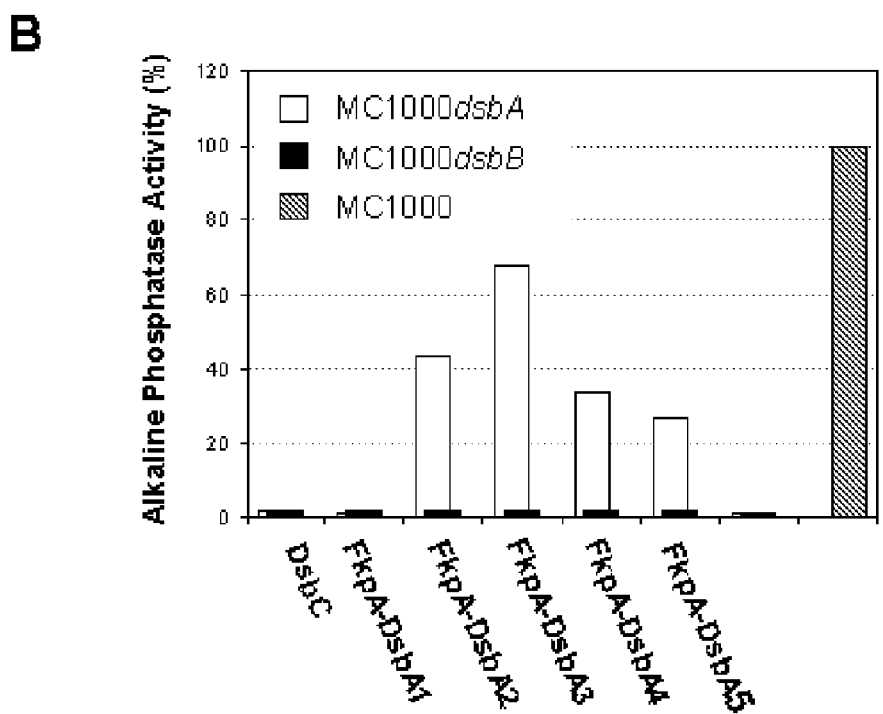
Figure 3:
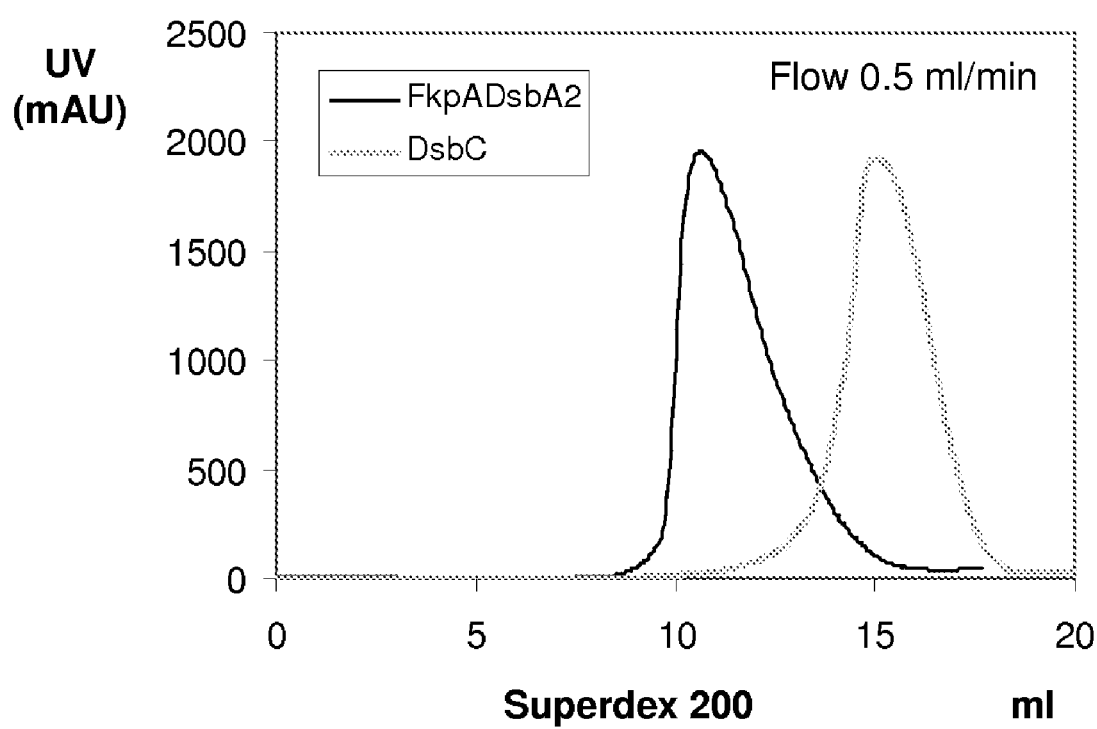
FIG. 3. Size-exclusion chromatograms of FkpADsbA2 and DsbC.

In vivo studies revealed that the FkpA-DsbA chimeras constructed are able to catalyze the rearrangement of nonnative disulfide bonds. Three of the enzymes, namely FkpA fused to the DsbA molecule starting from the $2^{nd}$, $3^{rd}$, and $4^{th}$ amino acid residues, were able to assist the folding of vtPA in the periplasm of E. coli to degrees comparable to the yield of active vtPA obtained overexpressing wild-type DsbC (FIG. 2A). Thus the constructed artificial enzymes are disulfide isomerases in vivo. Moreover, the ability of these artificial enzymes to act as isomerases was dependent on the presence of DsbD, demonstrating that their catalytic domains are able to interact with DsbD and depend on it for their recycling.

Although DsbD is able to reduce the monomeric DsbA extremely slowly in vitro (Rozhkova et al., 2004), the steric interactions created by dimerization of DsbA allow for the reduction of the artificial disulfide isomerases by DsbD in vivo. From gel filtration analysis of the purified proteins, it was observed that all the artificial disulfide isomerases are present exclusively as dimers. Because the in vivo folding of active vtPA was analyzed in an E. coli strain where DsbC is expressed in the periplasm from the chromosomal gene, the possibility that heterodimeric molecules generated by interaction between the dimerization domains of a wild-type DsbC monomer and of an FkpA-DsbA monomer has not been ruled out. However, the probability of this scenario is unlikely, in that the formation of such heterodimers would not significantly increase the yield of active vtPA with respect to the yield obtained in the background strain, in which the amount of periplasmic DsbC derives only from the chromosomal copy of the gene. In addition, the same study was performed in an overexpressing mutant of the FkpA-DsbA3 enzyme (with DsbC as a control), where the N-terminal cysteine in the CXXC active site was substituted with an alanine, to inactivate the oxidoreductase activity of the molecule. This substitution completely impaired the enzymes' ability to assist the in vivo folding of vtPA, thus the possibility that the high chaperone activity of FkpA is responsible for the folding of vtPA can be ruled out.

The ability of the artificial disulfide isomerases to simultaneously catalyze oxidase activity and rearrangement of non-native disulfides in vivo (i.e., assist the folding of vtPA in a dsbA⁻ background) was observed to be strictly correlated with their ability to complement for the lack of DsbA, and restore alkaline phosphatase activity. In other words, we showed that the catalysis of disulfide bond formation during the folding of vtPA in dsbA⁻ cells overexpressing the FkpA-DsbA chimeras could be attributed to their in vivo oxidase activity, in a DsbB-dependent fashion. For instance the artificial disulfide isomerase that displays the highest oxidase activity, FkpA-DsbA3, was also shown to assist the folding of vtPA in a dsbA background strain (FIG. 2A). This suggests that the particular nature of the linker joining the two domains in each monomer influences the orientation of the active sites allowing for the reduction by DsbD and oxidation by DsbB in the periplasm of the same cell. Likewise, the moderate degree of isomerase activity exhibited by FkpA-DsbA2 and FkpA-DsbA4 in a dsbA– background (FIG. 2A) is presumably due to the limited ability of these enzymes to be oxidized by DsbB (FIG. 2B). The nature of the α-helical linker may affect the orientation of the catalytic domains, and the propensity of the molecule to be oxidized by DsbB. As a result, since the degree of in vivo oxidation is correlated to the amount of protein found in the oxidized state in the periplasmic space, the ability of the enzymes to catalyze the folding of vtPA in a $dsbA^-$ strain is dependent on their oxidase activity.

Example 4

Expression, Purification, and in vitro Biochemical Assays of FkpA-DsbA Chimera Proteins For the purification of the FkpA-DsbA chimera proteins, the appropriate genes were cloned behind the T7 promoter in pET28(a), and the resulting plasmids were transformed into *E. coli* BL21(DE3). Protein expression and purification was performed as previously described (Segatori et al., 2004). The FkpA-DsbA2, FkpA-DsbA3, FkpA-DsbA4, and FkpA-DsbA5 chimeras, and DsbC as a control were purified by IMAC chromatography and their oligomerization status was analyzed by gel filtration FPLC. All the proteins eluted exclusively as dimers (e.g., FIG. 3). All proteins used in this study were more than 95% pure as judged by Coomassie Brilliant Blue-stained SDS-PAGE gels.

The rate of insulin reduction in the presence of DTT was determined as previously described (Holmgren 1979). The change of $A_{650}$ in the reaction was monitored as a direct measure of the aggregation of reduced insulin, and the activity is expressed as the ratio of the initial slope of the turbidity curve to the lag time (Martinez-Galisteo et al., 1995). The renaturation of reduced, denatured RNase A was determined as described by Lyles and Gilbert (Lyles and Gilbert, 1991). The protection of citrate synthase from thermal inactivation was monitored according to Buchner et al., 1998. The rate of thermal inactivation obtained with or without 0.4 μM of purified enzymes was determined.

Lack of DsbC has been reported to cause sensitivity to copper in *E. coli* (Hiniker et al., 2005). As shown in table 3, a dsbA-dsbC *E. coli* mutant strain lacking DsbC fails to grow in the presence of ≧4 mM $CuCl_2$. However, the presence of a chimeric FkpADsbA protein allowed growth in the presence of 5-8 mM $CuCl_2$.

TABLE 3

| Strain Relevant Genotype | Effect of $CuCl_2$: 0 mM $CuCl_2$ | 2 mM $CuCl_2$ | 3 mM $CuCl_2$ | 4 mM $CuCl_2$ | 5 mM $CuCl_2$ | 6 mM $CuCl_2$ | 7 mM $CuCl_2$ | 8 mM $CuCl_2$ |
|---|---|---|---|---|---|---|---|---|
| DHB4 | +++ | +++ | +++ | +++ | +++ | +++ | +++ | +++ |
| DHB4 dsbA– dsbC– | +++ | +++ | +++ | | | — | | |
| DHB4 dsbA– dsbC–, pBAD33-fkpAdsbA1 | +++ | +++ | +++ | | –– | | | |
| DHB4 dsbA– dsbC–, pBAD33-fkpAdsbA2 | +++ | +++ | +++ | +++ | +++ | +++ | +–– | +––– |
| DHB4 dsbA– dsbC–, pBAD33-fkpAdsbA3 | +++ | +++ | +++ | +++ | +++ | +_– | | |
| DHB4 dsbA– dsbC–, pBAD33-fkpAdsbA4 | +++ | +++ | +++ | +++ | +++ | | +–– | |
| DHB4 dsbA– dsbC–, pBAD33-fkpAdsbA5 | +++ | +++ | +++ | +++ | +++ | +___ | | |
| DHB4 dsbA– dsbC–, pBAD33-dsbC | +++ | +++ | +++ | +++ | +++ | +++ | +++ | +++ |
| DHB4 dsbA– dsbC–, pBAD33 | +++ | +++ | +++ | | | | | |

The intrinsic isomerase activity of the artificial disulfide isomerases was determined using RNase A as a substrate (Lyles and Gilbert, 1991). Interestingly, the artificial enzymes displayed low in vitro isomerase activity which was only 15-21% of that of DsbC (Table 4).

the overall three-dimensional structure of the artificial enzymes, and, as a result, in vitro, they act on the specific substrate used in this assay, insulin, as two monomeric DsbA. This suggests that the reduction of insulin may not be an accurate measure of the reductase activity on the periplasm.

TABLE 4

In vitro activities of purified enzymes

| Enzyme | RNAse Refolding*† μM/min/μM Enzyme | Insulin Reduction* $*10^3$ $D_{A650\ nm}$/min$^{-2}$ | Citrate Synthase Inactivation | |
|---|---|---|---|---|
| | | | CS $t_{1/2}$(min) | μ (min − 1) |
| — | — | — | 0.94 ± 0.01 | 0.51 ± 0.01 |
| DsbC | 0.067 ± 0.012 | 5.81 ± 0.21 | 3.15 ± 0.05 | 0.22 ± 0.02 |
| FkpA-DsbA2 | 0.012 ± 0.001 | 0.45 ± 0.11 | 2.46 ± 0.04 | 0.17 ± 0.06 |
| FkpA-DsbA3 | 0.013 ± 0.001 | 0.43 ± 0.13 | 2.01 ± 0.05 | 0.36 ± 0.06 |
| FkpA-DsbA4 | 0.014 ± 0.003 | 0.55 ± 0.12 | 3.82 ± 0.06 | 0.45 ± 0.22 |
| FkpA-DsbA5 | 0.01 ± 0.001 | 0.38 ± 0.16 | 2.71 ± 0.07 | 0.26 ± 0.09 |

This suggests that the artificial disulfide isomerases, similarly to the DsbC-DsbA chimeras (Segatori et al., 2004), might catalyze the rearrangement of non-native disulfides by cycles of reduction and oxidation of the substrate, rather than by mere catalysis of isomerization. As shown in FIG. 2B, FkpA-DsbA1 completely resists the oxidation by DsbB, and is therefore most likely present in the periplasm in a completely reduced state. In agreement with the conclusion suggested above, the yield of active vtPA observed when FkpA-DsbA1 is overexpressed in the periplasm of a dsbA+ bacterial strain is only slightly higher than the value obtained for the background strain. Likewise, FkpA-DsbA5 moderate oxidase activity is consistent with its limited isomerase activity in vivo. Finally, without wishing to be bound by any theory, the higher propensity of FkpA-DsbA2, FkpA-DsbA3, and FkpA-DsbA4 to be oxidized by DsbB suggests that the fraction of these enzymes present in the oxidized state is sufficient to catalyze the folding of vtPA in a dsbA+ strain through cycles of reduction and oxidation. However, in dsbA⁻ cells, the artificial disulfide isomerases need to catalyze both oxidation and rearrangement of disulfides. In this setting, the timing of oxidation and reduction cycles becomes more stringent, and, without being bound by any theory, it is proposed that the steric hindrance generated by the specific orientation of the catalytic domains in the FkpA-DsbA2 and FkpA-DsbA4 molecules (as opposed to FkpA-DsbA3) delays the interaction with the substrate, or the recycling by DsbB and DsbD, resulting in sub-optimal timing of in vivo folding.

The in vitro insulin reduction activity (Zhao et al., 2003) of the FkpA-DsbA chimeras was 7-10% of that of DsbC (Table 4). For comparison, DsbA has about 10% of the activity of DsbC in this assay (Segatori et al., 2004). All the chimeras exhibited low disulfide isomerase activity in the refolding of reduced RNAse A. FkpA-DsbA2, FkpA-DsbA3, FkpA-DsbA4, and FkpA-DsbA5, and DsbCdαN-TrxA displayed from 15 to 21% of the isomerase activity of DsbC, which in turn was 8-fold less active than protein disulfide-isomerase (PDI; EC 5.3.4.1). Without wishing to be bound by theory, one explanation is that because the α-helical linker in the FkpA-DsbA molecules is considerably longer than that of DsbC, the two catalytic domains are kept more separated in Similarly to what was observed in the refolding of RNAse A, the reduction of insulin is a measurement of the enzymes reductase activity per se, which therefore does not consider the outcome of possible in vivo interactions.

Analysis of the artificial molecules in vitro chaperone activity was performed using citrate synthase as a substrate, and monitoring the ability of the artificial enzymes to prevent the inactivation of citrate synthase by thermal denaturation (Table 4). The chaperone activity of all of the artificial disulfide bond isomerases was found to be comparable to that of DsbC. The half-life of denatured CS is used as an indication of the enzyme chaperone activity. At a 2.7 fold stoichiometric excess, the half-life of CS incubated with FkpA-DsbA2, FkpA-DsbA3, FkpA-DsbA4, and FkpA-DsbA5 was observed to be respectively 0.8, 0.6, 1.2, and 0.9-fold the value obtained using DsbC as a chaperone (Table 4).

Example 5

Complementation of DsbA Activity by FkpA-DsbA Chimera Molecules

The catalytic domain of the FkpA-DsbA chimera polypeptides is represented by the DsbA portion of the polypeptide. This raises the possibility that these molecules could simultaneously catalyze the oxidation and the rearrangement of non-native disulfide bonds in dsbA cells, lacking DsbA. The folding of vtPA, in addition to requiring the overexpression of DsbC, is also dependent on the presence of a protein oxidant, namely DsbA. Therefore, in strain SF100 (Baneyx and Georgiou, 1990) lacking DsbA, only background levels of active vtPA are observed. Multicopy expression of DsbC, in this strain background, also failed to yield active vtPA, since DsbC cannot serve as an efficient protein oxidant (FIG. 2A). In contrast, it was found that expression of one of the artificial disulfide isomerases, FkpA-DsbA3, afforded the same yield of active vtPA in cells with or without DsbA. The level of vtPA activity in this case was 13-fold higher than in dsbA cells without plasmid. Thus, activity of this hybrid isomerase variant was not affected by the absence of DsbA. The other FkpA-DsbA chimeras showed weak vtPA folding activity in dsbA cells (FIG. 2A).

To verify that the ability of the chimeras to assist the folding of vtPA in a dsbA background depends on these molecules' oxidase activity, their ability to complement the phenotypes caused by the absence of DsbA was examined. In particular, dsbA mutant strains display very low alkaline phosphatase (PhoA) activity. Similarly to DsbC, FkpA-DsbA1 which did not give vtPA activity above background in a dsbA host was also not able to catalyze the formation of enzymatically active PhoA in MC4100 dsbA cells (FIG. 2B). However, the other four FkpA-DsbA variants were able to support protein oxidation to various degrees. In E. coli MC1000 dsbA grown in low phosphate media, the PhoA activity is 30-fold lower than in its isogenic parent. Co-expression of FkpA-DsbA2, FkpA-DsbA3, FkpA-DsbA4, and FkpA-DsbA5 restored PhoA activity to respectively 43, 67, 35, and 28% of the value obtained in the parental strain MC1000 (FIG. 2B). None of the FkpA-DsbA chimeras could restore PhoA activity in dsbB cells (FIG. 2B), suggesting that the oxidase activity observed in dsbA cells is dependent on the oxidation of the FkpA-DsbA chimeras by DsbB.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,683,195
U.S. Pat. No. 5,304,472
U.S. Pat. No. 5,342,763
U.S. Pat. No. 5,023,171
U.S. Pat. No. 5,639,635
U.S. Pat. No. 5,789,199
U.S. Pat. No. 6,083,715
U.S. Pat. No. 6,673,569
Aiyar et al., *Methods Mol. Biol.*, 57:177-191, 1996.
Arie et al., *Mol. Microbiol.*, 39:199-210, 2001.
Australian Appl. AU 61804/86
Baneyx and Georgiou, *J. Bacteriol.*, 172:491-494, 1990.
Baneyx, and Mujacic, *Nat. Biotechnol.*, 22:1399-1408, 2004
Bardwell et al., *Mol. Microbiol.*, 14:199-205, 1994.
Bardwell et al., *Proc. Nat. Acad. Sci. USA*, 90:1038-1042, 1993.
Behrens et al., *EMBO J.* 20:285-294, 2001.
Berkmen et al., *J. Biol. Chem.*, 280:11387-11394, 2005.
Bessette et al., *Proc. Nat. Acad. Sci. USA*, 96:13703-13708, 1999.
Bessette et al., *J. Bacteriol.* 183:980-988, 2001.
Bolivar, et al., *Gene* 2:95-113, 1977.
Brickman and Beckwith, *J. Mol. Biol.*, 96:307-316, 1975.
Buchner et al., *Methods Enzymol.*, 290:323-338, 1998.
Carter et al., *Nucleic Acids Res.* 13:4431-4443, 1985.
Casadaban et al. *J. Mol. Biol.* 138:179-207, 1980.
Chang, et al. *Nature* 275:617-624, 1978.
Collet and Bardwell, *Mol. Microbiol.*, 44:1-8, 2002.
Couvreur et al., *FEBS Lett.*, 84(2):323-326, 1977.
European Appl. EP 0382174
European Appl. EP 196920
European Appl. EP 207589
European Appl. EP 231624
European Appl. EP 24208
European Appl. EP 263172
European Appl. EP 289508
European Appl. EP 292009
European Appl. EP 297066
European Appl. EP 302456
European Appl. EP 34051
European Appl. EP 352119
European Appl. EP 36776
European Appl. EP 379890
Gabizon and Papahadjopoulos, *Proc. Natl. Acad. Sci. USA*, 85(18):6949-6953, 1988.
Goeddel et al., *Proc. Natl. Acad. Sci. USA*, 76(1):106-110, 1979.
Goeddel, *Nucleic Acids Res.*, 8:4057-4074, 1980.
Goeddel, et al. in *Gene Expression Technology* vol. 185 Elsevier, 1990.
Grunfeld et al., *Appl. Biochem. Biotechnol.*, 33(2): 117-138, 1992.
Guzman et al., *J. Bacteriol.*, 177:4121-4130, 1995.
Harlow and Lane, In: *Antibodies: A Laboratory Manual*, Cold Spring Harbor Laboratory, Cold Spring Harbor, N.Y., 346-348, 1988.
Hiniker et al., *J. Biol. Chem.* 280:33785-33791, 2005.
Holmgren, *J. Biol. Chem.*, 254:9627-9632, 1979.
Horne et al., *Arch. Microbiol.*, 163: 357-365, 1995.
Isaki et al., *J. Bacteriol.*, 172:6512-6517, 1990.
Joly et al., *Biochemistry*, 36:10067-10072, 1997.
Joly et al., *Proc. Natl. Acad. Sci. USA*, 95:2773-2777, 1998.
Kadokura et al., *Annu. Rev. Biochem.*, 72:111-135, 2003.
Kim and Swartz, *Biotechnol. Bioeng.*, 85:122-129, 2004.
Kloek et al., *Molec. Plant Pathol.*, 1:139-150, 2000.
Kurokawa et al., *J. Biol. Chem.*, 276:14393-14399, 2001.
Kyte and Doolittle, *J. Mol. Biol.*, 157(1):105-132, 1982.
Lyles and Gilbert, *Biochemistry*, 30:613-619, 1991.
Maniatis et al., In: *Molecular Cloning*, A Laboratory Manual. Cold Spring Harbor Laboratory Press, Cold Spring Harbor, N.Y., 1982.
Martinez-Galisteo et al., *Comp. Biochem. Physiol. B Biochem. Mol. Biol.*, 111:17-25, 1995.
Masip et al., *Science* 303:1185-1189, 2004.
McBride et al., *Infect Immun.*, 70:2700-2703, 2002.
Missiakis et al., *EMBO J.*, 13:2013-2020, 1994.
PCT Appl. WO/93/24635
Qiu et al., *Appl. Environ. Microbiol.*, 64:4891-4896, 1998.
Ramm and Pluckthun, *J. Mol. Biol.*, 310:485-498, 2001.
Rozhkova et al., *Embo. J.*, 23:1709-1719, 2004.
Sambrook, et al., In: *Molecular Cloning*, A Laboratory Manual, 2nd Edition. Cold Spring Harbor Laboratory Press, N.Y., 1989.
Saul et al., *J. Mol. Biol.*, 335:595-608, 2004.
Segatori et al., *Proc. Natl. Acad. Sci. USA*, 101:10018-10023, 2004.
Shevchik et al., *Mol. Microbiol.*, 16:745-753, 1995.
Siebenlist et al. *Cell* 20:269, 1980.
Spoerel et al., *Methods Enzymol.*, 152:588-597, 1987.
Suzuki et al., *J. Cardiovasc. Pharmacol.*, 22:834-840, 1993.
Thomas, P., *Proc. Natl. Acad. Sci. USA.* 77:5201-5205, 1980.
Zapun et al. *Biochemistry*, 34:5075-5089, 1995.
Zapun et al., *Biochemistry*, 32:5083-5092, 1993.
Zhao et al., *J. Biol. Chem.*, 278:43292-43298, 2003.

What is claimed is:

1. An isolated nucleic acid molecule encoding a chimeric polypeptide comprising:
   a) a first DNA segment encoding a FkpA polypeptide, wherein the FkpA polypeptide allows for dimerization and provides a substrate binding region; and
   b) a second DNA segment encoding a DsbA polypeptide;
   wherein the first and second DNA segments are linked 5' to 3'; and wherein the chimeric polypeptide comprises one or more activities selected from the group consisting of: disulfide bond reduction activity, disulfide bond oxidation activity, disulfide bond isomerization activity, and chaperone activity.

2. The isolated nucleic acid molecule of claim 1, wherein the first DNA segment has from about 80% to about 99% sequence identity with SEQ ID NO:1.

3. The isolated nucleic acid molecule of claim 2, wherein the first DNA segment encodes a polypeptide comprising SEQ ID NO:2.

4. The isolated nucleic acid molecule of claim 1, wherein the second DNA segment encodes a polypeptide comprising SEQ ID NO:3.

5. The isolated nucleic acid molecule of claim 1, wherein the chimeric polypeptide comprises a sequence selected from the group consisting of SEQ ID NO:4, SEQ ID NO:5, SEQ ID NO:6, SEQ ID NO:7, and SEQ ID NO:8.

6. An expression construct comprising the nucleic acid molecule of claim 1 and a DNA segment encoding a polypeptide comprising at least two disulfide bonds.

7. An isolated host cell comprising the nucleic acid molecule of claim 1.

8. The host cell of claim 7, wherein the host cell is a gram negative or a gram positive bacterial cell.

9. The host cell of claim 7, wherein the host cell is an *Escherichia coli* cell.

10. The host cell of claim 7, wherein the host cell expresses at least one of DsbD and DsbB.

11. A method for producing a biologically active heterologous polypeptide in a host cell comprising:
    a) culturing isolated host cells in a culture medium, wherein the host cells comprise both the nucleic acid molecule of claim 1 and a second nucleic acid molecule that encodes a heterologous polypeptide which comprises at least two disulfide bonds in its native form;
    b) expressing the nucleic acid molecule of claim 1 and the second nucleic acid molecule in the host cells under conditions effective to produce said chimeric polypeptide, and said heterologous polypeptide and;
    c) isolating the heterologous polypeptide.

12. The method of claim 11, wherein the heterologous polypeptide is selected from the group consisting of human tPA; vtPA, RNAse A, and PhoA.

13. The method of claim 11, wherein the host cells are bacterial cells.

14. The method of claim 13, wherein the bacterial cells express DsbD and DsbB.

15. The method of claim 13, wherein the bacterial cells are gram-negative bacterial cells.

16. The method of claim 15, wherein the bacterial cells are *E. coli* cells.

17. The method of claim 11, wherein the heterologous polypeptide is operatively linked to a signal sequence that functions to cause secretion of the polypeptide from the host cell cytoplasm.

18. The method of claim 17, wherein the signal sequence comprises OmpA, Lpp, LamB, MalE, PelB, or StII.

19. The method of claim 11, wherein the nucleic acid molecule of claim 1 and the second nucleic acid molecule are both expressed by a single host cell.

20. The method of claim 11, wherein the nucleic acid molecule of claim 1 and the second nucleic acid molecule are expressed by separate host cells.

21. The method of claim 11, wherein the heterologous polypeptide is isolated from the culture medium of the host cells.

* * * * *

SEQUENCE LISTING

<160> NUMBER OF SEQ ID NOS: 45

<210> SEQ ID NO 1
<211> LENGTH: 270
<212> TYPE: PRT
<213> ORGANISM: Escherichia coli

<400> SEQUENCE: 1

Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
            20                  25                  30

Thr Ala Ala Asp Ser Lys Ala Ala Phe Lys Asn Asp Asp Gln Lys Ser
        35                  40                  45

Ala Tyr Ala Leu Gly Ala Ser Leu Gly Arg Tyr Met Glu Asn Ser Leu
    50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
    130                 135                 140

Ser Thr Gly Leu Val Tyr Gln Val Val Glu Ala Gly Lys Gly Glu Ala
145                 150                 155                 160

Pro Lys Asp Ser Asp Thr Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205

Ile Lys Lys Gly Gly Lys Ile Lys Leu Val Ile Pro Pro Glu Leu Ala
    210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
            260                 265                 270

<210> SEQ ID NO 2
<211> LENGTH: 114
<212> TYPE: PRT
<213> ORGANISM: Escherichia coli

<400> SEQUENCE: 2

Met Lys Lys Gly Phe Met Leu Phe Thr Leu Leu Ala Ala Phe Ser Gly
1               5                   10                  15

Phe Ala Gln Ala Gln Lys Ser Ala Tyr Ala Leu Gly Ala Ser Leu Gly
            20                  25                  30

Arg Tyr Met Glu Asn Ser Leu Lys Glu Gln Glu Lys Leu Gly Ile Lys
        35                  40                  45

```
Leu Asp Lys Asp Gln Leu Ile Ala Gly Val Gln Asp Ala Phe Ala Asp
 50                  55                  60

Lys Ser Lys Leu Ser Asp Gln Glu Ile Glu Gln Thr Leu Gln Ala Phe
 65                  70                  75                  80

Glu Ala Arg Val Lys Ser Ser Ala Gln Ala Lys Met Glu Lys Asp Ala
                 85                  90                  95

Ala Asp Asn Glu Ala Lys Gly Lys Glu Tyr Arg Glu Lys Phe Ala Lys
            100                 105                 110

Glu Lys

<210> SEQ ID NO 3
<211> LENGTH: 189
<212> TYPE: PRT
<213> ORGANISM: Escherichia coli

<400> SEQUENCE: 3

Ala Gln Tyr Glu Asp Gly Lys Gln Tyr Thr Thr Leu Glu Lys Pro Val
 1               5                  10                  15

Ala Gly Ala Pro Gln Val Leu Glu Phe Phe Ser Phe Phe Cys Pro His
                20                  25                  30

Cys Tyr Gln Phe Glu Glu Val Leu His Ile Ser Asp Asn Val Lys Lys
            35                  40                  45

Lys Leu Pro Glu Gly Val Lys Met Thr Lys Tyr His Val Asn Phe Met
 50                  55                  60

Gly Gly Asp Leu Gly Lys Asp Leu Thr Gln Ala Trp Ala Val Ala Met
 65                  70                  75                  80

Ala Leu Gly Val Glu Asp Lys Val Thr Val Pro Leu Phe Glu Gly Val
                 85                  90                  95

Gln Lys Thr Gln Thr Ile Arg Ser Ala Ser Asp Ile Arg Asp Val Phe
            100                 105                 110

Ile Asn Ala Gly Ile Lys Gly Glu Glu Tyr Asp Ala Ala Trp Asn Ser
            115                 120                 125

Phe Val Val Lys Ser Leu Val Ala Gln Gln Glu Lys Ala Ala Ala Asp
130                 135                 140

Val Gln Leu Arg Gly Val Pro Ala Met Phe Val Asn Gly Lys Tyr Gln
145                 150                 155                 160

Leu Asn Pro Gln Gly Met Asp Thr Ser Asn Met Asp Val Phe Val Gln
                165                 170                 175

Gln Tyr Ala Asp Thr Val Lys Tyr Leu Ser Glu Lys Lys
            180                 185

<210> SEQ ID NO 4
<211> LENGTH: 309
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Met Lys Lys Gly Phe Met Leu Phe Thr Leu Leu Ala Ala Phe Ser Gly
 1               5                  10                  15

Phe Ala Gln Ala Gln Lys Ser Ala Tyr Ala Leu Gly Ala Ser Leu Gly
                20                  25                  30

Arg Tyr Met Glu Asn Ser Leu Lys Glu Gln Glu Lys Leu Gly Ile Lys
            35                  40                  45
```

```
Leu Asp Lys Asp Gln Leu Ile Ala Gly Val Gln Asp Ala Phe Ala Asp
     50                  55                  60

Lys Ser Lys Leu Ser Asp Gln Glu Ile Glu Gln Thr Leu Gln Ala Phe
 65                  70                  75                  80

Glu Ala Arg Val Lys Ser Ser Gln Ala Lys Met Glu Lys Asp Ala
                 85                  90                  95

Ala Asp Asn Glu Ala Lys Gly Lys Glu Tyr Arg Glu Lys Phe Ala Lys
             100                 105                 110

Glu Lys Ala Gln Tyr Glu Asp Gly Lys Gln Tyr Thr Thr Leu Glu Lys
         115                 120                 125

Pro Val Ala Gly Ala Pro Gln Val Leu Glu Phe Phe Ser Phe Phe Cys
     130                 135                 140

Pro His Cys Tyr Gln Phe Glu Glu Val Leu His Ile Ser Asp Asn Val
145                 150                 155                 160

Lys Lys Lys Leu Pro Glu Gly Val Lys Met Thr Lys Tyr His Val Asn
                 165                 170                 175

Phe Met Gly Gly Asp Leu Gly Lys Asp Leu Thr Gln Ala Trp Ala Val
             180                 185                 190

Ala Met Ala Leu Gly Val Glu Asp Lys Val Thr Val Pro Leu Phe Glu
         195                 200                 205

Gly Val Gln Lys Thr Gln Thr Ile Arg Ser Ala Ser Asp Ile Arg Asp
     210                 215                 220

Val Phe Ile Asn Ala Gly Ile Lys Gly Glu Glu Tyr Asp Ala Ala Trp
225                 230                 235                 240

Asn Ser Phe Val Val Lys Ser Leu Val Ala Gln Gln Glu Lys Ala Ala
                 245                 250                 255

Ala Asp Val Gln Leu Arg Gly Val Pro Ala Met Phe Val Asn Gly Lys
             260                 265                 270

Tyr Gln Leu Asn Pro Gln Gly Met Asp Thr Ser Asn Met Asp Val Phe
         275                 280                 285

Val Gln Gln Tyr Ala Asp Thr Val Lys Tyr Leu Ser Glu Lys Lys His
     290                 295                 300

His His His His His
305

<210> SEQ ID NO 5
<211> LENGTH: 308
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Met Lys Lys Gly Phe Met Leu Phe Thr Leu Leu Ala Ala Phe Ser Gly
  1               5                  10                  15

Phe Ala Gln Ala Gln Lys Ser Ala Tyr Ala Leu Gly Ala Ser Leu Gly
             20                  25                  30

Arg Tyr Met Glu Asn Ser Leu Lys Glu Gln Glu Lys Leu Gly Ile Lys
         35                  40                  45

Leu Asp Lys Asp Gln Leu Ile Ala Gly Val Gln Asp Ala Phe Ala Asp
     50                  55                  60

Lys Ser Lys Leu Ser Asp Gln Glu Ile Glu Gln Thr Leu Gln Ala Phe
 65                  70                  75                  80

Glu Ala Arg Val Lys Ser Ser Gln Ala Lys Met Glu Lys Asp Ala
                 85                  90                  95
```

```
Ala Asp Asn Glu Ala Lys Gly Lys Glu Tyr Arg Glu Lys Phe Ala Lys
            100                 105                 110

Glu Lys Gln Tyr Glu Asp Gly Lys Gln Tyr Thr Thr Leu Glu Lys Pro
        115                 120                 125

Val Ala Gly Ala Pro Gln Val Leu Glu Phe Phe Ser Phe Phe Cys Pro
    130                 135                 140

His Cys Tyr Gln Phe Glu Glu Val Leu His Ile Ser Asp Asn Val Lys
145                 150                 155                 160

Lys Lys Leu Pro Glu Gly Val Lys Met Thr Lys Tyr His Val Asn Phe
            165                 170                 175

Met Gly Gly Asp Leu Gly Lys Asp Leu Thr Gln Ala Trp Ala Val Ala
        180                 185                 190

Met Ala Leu Gly Val Glu Asp Lys Val Thr Val Pro Leu Phe Glu Gly
    195                 200                 205

Val Gln Lys Thr Gln Thr Ile Arg Ser Ala Ser Asp Ile Arg Asp Val
    210                 215                 220

Phe Ile Asn Ala Gly Ile Lys Gly Glu Glu Tyr Asp Ala Ala Trp Asn
225                 230                 235                 240

Ser Phe Val Val Lys Ser Leu Val Ala Gln Gln Lys Ala Ala Ala
            245                 250                 255

Asp Val Gln Leu Arg Gly Val Pro Ala Met Phe Val Asn Gly Lys Tyr
        260                 265                 270

Gln Leu Asn Pro Gln Gly Met Asp Thr Ser Asn Met Asp Val Phe Val
    275                 280                 285

Gln Gln Tyr Ala Asp Thr Val Lys Tyr Leu Ser Glu Lys Lys His His
    290                 295                 300

His His His His
305

<210> SEQ ID NO 6
<211> LENGTH: 307
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Met Lys Lys Gly Phe Met Leu Phe Thr Leu Leu Ala Ala Phe Ser Gly
1               5                   10                  15

Phe Ala Gln Ala Gln Lys Ser Ala Tyr Ala Leu Gly Ala Ser Leu Gly
            20                  25                  30

Arg Tyr Met Glu Asn Ser Leu Lys Glu Gln Glu Lys Leu Gly Ile Lys
        35                  40                  45

Leu Asp Lys Asp Gln Leu Ile Ala Gly Val Gln Asp Ala Phe Ala Asp
    50                  55                  60

Lys Ser Lys Leu Ser Asp Gln Glu Ile Glu Gln Thr Leu Gln Ala Phe
65                  70                  75                  80

Glu Ala Arg Val Lys Ser Ser Ala Gln Ala Lys Met Glu Lys Asp Ala
                85                  90                  95

Ala Asp Asn Glu Ala Lys Gly Lys Glu Tyr Arg Glu Lys Phe Ala Lys
            100                 105                 110

Glu Lys Tyr Glu Asp Gly Lys Gln Tyr Thr Thr Leu Glu Lys Pro Val
        115                 120                 125

Ala Gly Ala Pro Gln Val Leu Glu Phe Phe Ser Phe Phe Cys Pro His
```

```
            130                 135                 140
Cys Tyr Gln Phe Glu Glu Val Leu His Ile Ser Asp Asn Val Lys Lys
145                 150                 155                 160

Lys Leu Pro Glu Gly Val Lys Met Thr Lys Tyr His Val Asn Phe Met
                165                 170                 175

Gly Gly Asp Leu Gly Lys Asp Leu Thr Gln Ala Trp Ala Val Ala Met
            180                 185                 190

Ala Leu Gly Val Glu Asp Lys Val Thr Val Pro Leu Phe Glu Gly Val
            195                 200                 205

Gln Lys Thr Gln Thr Ile Arg Ser Ala Ser Asp Ile Arg Asp Val Phe
210                 215                 220

Ile Asn Ala Gly Ile Lys Gly Glu Glu Tyr Asp Ala Ala Trp Asn Ser
225                 230                 235                 240

Phe Val Val Lys Ser Leu Val Ala Gln Gln Glu Lys Ala Ala Ala Asp
                245                 250                 255

Val Gln Leu Arg Gly Val Pro Ala Met Phe Val Asn Gly Lys Tyr Gln
            260                 265                 270

Leu Asn Pro Gln Gly Met Asp Thr Ser Asn Met Asp Val Phe Val Gln
            275                 280                 285

Gln Tyr Ala Asp Thr Val Lys Tyr Leu Ser Glu Lys His His His
    290                 295                 300

His His His
305

<210> SEQ ID NO 7
<211> LENGTH: 306
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Met Lys Lys Gly Phe Met Leu Phe Thr Leu Leu Ala Ala Phe Ser Gly
1               5                   10                  15

Phe Ala Gln Ala Gln Lys Ser Ala Tyr Ala Leu Gly Ala Ser Leu Gly
                20                  25                  30

Arg Tyr Met Glu Asn Ser Leu Lys Glu Gln Lys Leu Gly Ile Lys
            35                  40                  45

Leu Asp Lys Asp Gln Leu Ile Ala Gly Val Gln Asp Ala Phe Ala Asp
    50                  55                  60

Lys Ser Lys Leu Ser Asp Gln Glu Ile Glu Gln Thr Leu Gln Ala Phe
65                  70                  75                  80

Glu Ala Arg Val Lys Ser Ser Ala Gln Ala Lys Met Glu Lys Asp Ala
                85                  90                  95

Ala Asp Asn Glu Ala Lys Gly Lys Glu Tyr Arg Glu Lys Phe Ala Lys
            100                 105                 110

Glu Lys Glu Asp Gly Lys Gln Tyr Thr Thr Leu Glu Lys Pro Val Ala
        115                 120                 125

Gly Ala Pro Gln Val Leu Glu Phe Phe Ser Phe Phe Cys Pro His Cys
    130                 135                 140

Tyr Gln Phe Glu Glu Val Leu His Ile Ser Asp Asn Val Lys Lys
145                 150                 155                 160

Leu Pro Glu Gly Val Lys Met Thr Lys Tyr His Val Asn Phe Met Gly
                165                 170                 175
```

```
Gly Asp Leu Gly Lys Asp Leu Thr Gln Ala Trp Ala Val Ala Met Ala
            180                 185                 190

Leu Gly Val Glu Asp Lys Val Thr Val Pro Leu Phe Glu Gly Val Gln
        195                 200                 205

Lys Thr Gln Thr Ile Arg Ser Ala Ser Asp Ile Arg Asp Val Phe Ile
210                 215                 220

Asn Ala Gly Ile Lys Gly Glu Glu Tyr Asp Ala Ala Trp Asn Ser Phe
225                 230                 235                 240

Val Val Lys Ser Leu Val Ala Gln Gln Glu Lys Ala Ala Ala Asp Val
                245                 250                 255

Gln Leu Arg Gly Val Pro Ala Met Phe Val Asn Gly Lys Tyr Gln Leu
            260                 265                 270

Asn Pro Gln Gly Met Asp Thr Ser Asn Met Asp Val Phe Val Gln Gln
        275                 280                 285

Tyr Ala Asp Thr Val Lys Tyr Leu Ser Glu Lys His His His His His
    290                 295                 300

His His
305

<210> SEQ ID NO 8
<211> LENGTH: 305
<212> TYPE: PRT
<213> ORGANISM: Escherichia coli

<400> SEQUENCE: 8

Met Lys Lys Gly Phe Met Leu Phe Thr Leu Leu Ala Ala Phe Ser Gly
 1               5                   10                  15

Phe Ala Gln Ala Gln Lys Ser Ala Tyr Ala Leu Gly Ala Ser Leu Gly
                20                  25                  30

Arg Tyr Met Glu Asn Ser Leu Lys Glu Gln Glu Lys Leu Gly Ile Lys
            35                  40                  45

Leu Asp Lys Asp Gln Leu Ile Ala Gly Val Gln Asp Ala Phe Ala Asp
        50                  55                  60

Lys Ser Lys Leu Ser Asp Gln Glu Ile Glu Gln Thr Leu Gln Ala Phe
 65                 70                  75                  80

Glu Ala Arg Val Lys Ser Ser Ala Gln Ala Lys Met Glu Lys Asp Ala
                85                  90                  95

Ala Asp Asn Glu Ala Lys Gly Lys Glu Tyr Arg Glu Lys Phe Ala Lys
            100                 105                 110

Glu Lys Asp Gly Lys Gln Tyr Thr Thr Leu Glu Lys Pro Val Ala Gly
        115                 120                 125

Ala Pro Gln Val Leu Glu Phe Phe Ser Phe Phe Cys Pro His Cys Tyr
130                 135                 140

Gln Phe Glu Glu Val Leu His Ile Ser Asp Asn Val Lys Lys Lys Leu
145                 150                 155                 160

Pro Glu Gly Val Lys Met Thr Lys Tyr His Val Asn Phe Met Gly Gly
                165                 170                 175

Asp Leu Gly Lys Asp Leu Thr Gln Ala Trp Ala Val Ala Met Ala Leu
            180                 185                 190

Gly Val Glu Asp Lys Val Thr Val Pro Leu Phe Glu Gly Val Gln Lys
        195                 200                 205

Thr Gln Thr Ile Arg Ser Ala Ser Asp Ile Arg Asp Val Phe Ile Asn
    210                 215                 220

Ala Gly Ile Lys Gly Glu Glu Tyr Asp Ala Ala Trp Asn Ser Phe Val
225                 230                 235                 240
```

Val Lys Ser Leu Val Ala Gln Gln Glu Lys Ala Ala Asp Val Gln
            245                 250                 255

Leu Arg Gly Val Pro Ala Met Phe Val Asn Gly Lys Tyr Gln Leu Asn
        260                 265                 270

Pro Gln Gly Met Asp Thr Ser Asn Met Asp Val Phe Val Gln Gln Tyr
    275                 280                 285

Ala Asp Thr Val Lys Tyr Leu Ser Glu Lys Lys His His His His
290                 295                 300

His
305

<210> SEQ ID NO 9

<400> SEQUENCE: 9

000

<210> SEQ ID NO 10

<400> SEQUENCE: 10

000

<210> SEQ ID NO 11
<211> LENGTH: 930
<212> TYPE: DNA
<213> ORGANISM: Artificial Sequence
<220> FEATURE:
<223> OTHER INFORMATION: Description of Artificial Sequence: Synthetic

<400> SEQUENCE: 11
atgaagaaag gttttatgtt gtttactttg ttagcggcgt tttcaggctt tgctcaggct      60
cagaaatcag cttatgcact gggtgcctcg ctgggtcgtt acatggaaaa ctctctaaaa     120
gaacaagaaa aactgggcat caaactggat aaagatcagc tgatcgctgg tgttcaggat     180
gcatttgctg ataagagcaa actctccgac caagagatcg aacagactct acaagcattc     240
gaagctcgcg tgaagtcttc tgctcaggcg aagatggaaa agacgcggc tgataacgaa      300 gcaaaaggta agagtaccg cgagaaattt gccaaagaga aagcgcagta tgaagatggt      360
aaacagtaca ctaccctgga aaaccggta gctggcgcgc cgcaagtgct ggagttttc      420 tctttcttct gcccgcactg ctatcagttt gaagaagttc tgcatatttc tgataatgtg     480
aagaaaaaac tgccggaagg cgtgaagatg actaaatacc acgtcaactt catgggtggt     540
gacctgggca agatctgac tcaggcatgg gctgtggcga tggcgctggg cgtggaagac     600
aaagtgactg ttccgctgtt tgaaggcgta cagaaacccc agaccattcg ttctgcttct     660
gatatccgcg atgtatttat caacgcaggt attaaggtg aagagtacga cgcggcgtgg      720
aacagcttcg tggtgaaatc tctggtcgct cagcaggaaa agctgcagc tgacgtgcaa      780 ttgcgtggcg ttccggcgat gtttgttaac ggtaaatatc agctgaatcc gcagggtatg     840
gataccagca atatggatgt ttttgttcag cagtatgctg acacagtgaa atatctgtcc     900
gagaaaaaac accaccacca ccaccactaa                                     930

<210> SEQ ID NO 12
<211> LENGTH: 927
<212> TYPE: DNA
<213> ORGANISM: Artificial Sequence
<220> FEATURE:
<223> OTHER INFORMATION: Description of Artificial Sequence: Synthetic

<400> SEQUENCE: 12

```
atgaagaaag gttttatgtt gtttactttg ttagcggcgt tttcaggctt tgctcaggct    60
cagaaatcag cttatgcact gggtgcctcg ctgggtcgtt acatggaaaa ctctctaaaa   120
gaacaagaaa aactgggcat caaactggat aaagatcagc tgatcgctgg tgttcaggat   180
gcatttgctg ataagagcaa actctccgac caagagatcg aacagactct acaagcattc   240
gaagctcgcg tgaagtcttc tgctcaggcg aagatggaaa agacgcggc tgataacgaa    300
gcaaaaggta agagtaccg cgagaaattt gccaaagaga acagtatga agatggtaaa    360
cagtacacta ccctggaaaa accggtagct ggcgcgccgc aagtgctgga gttttctct    420
ttcttctgcc cgcactgcta tcagtttgaa gaagttctgc atatttctga taatgtgaag   480
aaaaaactgc cggaaggcgt gaagatgact aaataccacg tcaacttcat gggtggtgac   540
ctgggcaaag atctgactca ggcatgggct gtggcgatgg cgctgggcgt ggaagacaaa   600
gtgactgttc cgctgtttga aggcgtacag aaaacccaga ccattcgttc tgcttctgat   660
atccgcgatg tatttatcaa cgcaggtatt aaaggtgaag agtacgacgc ggcgtggaac   720
agcttcgtgg tgaaatctct ggtcgctcag caggaaaaag ctgcagctga cgtgcaattg   780
cgtggcgttc cggcgatgtt tgttaacggt aaatatcagc tgaatccgca gggtatggat   840
accagcaata tggatgtttt tgttcagcag tatgctgata cagtgaaata tctgtccgag   900
aaaaaacacc accaccacca ccactaa                                       927
```

<210> SEQ ID NO 13
<211> LENGTH: 924
<212> TYPE: DNA
<213> ORGANISM: Artificial Sequence
<220> FEATURE:
<223> OTHER INFORMATION: Description of Artificial Sequence: Synthetic

<400> SEQUENCE: 13

```
atgaagaaag gttttatgtt gtttactttg ttagcggcgt tttcaggctt tgctcaggct    60
cagaaatcag cttatgcact gggtgcctcg ctgggtcgtt acatggaaaa ctctctaaaa   120
gaacaagaaa aactgggcat caaactggat aaagatcagc tgatcgctgg tgttcaggat   180
gcatttgctg ataagagcaa actctccgac caagagatcg aacagactct acaagcattc   240
gaagctcgcg tgaagtcttc tgctcaggcg aagatggaaa agacgcggc tgataacgaa    300
gcaaaaggta agagtaccg cgagaaattt gccaaagaga atatgaaga tggtaaacag    360
tacactaccc tggaaaaacc ggtagctggc gcgccgcaag tgctggagtt tttctctttc   420
ttctgcccgc actgctatca gtttgaagaa gttctgcata tttctgataa tgtgaagaaa   480
aaactgccgg aaggcgtgaa gatgactaaa taccacgtca acttcatggg tggtgacctg   540
ggcaaagatc tgactcaggc atgggctgtg gcgatggcgc tgggcgtgga agacaaagtg   600
actgttccgc tgtttgaagg cgtacagaaa acccagacca ttcgttctgc ttctgatatc   660
cgcgatgtat ttatcaacgc aggtattaaa ggtgaagagt acgacgcggc gtggaacagc   720
ttcgtggtga atctctggt cgctcagcag gaaaaagctg cagctgacgt gcaattgcgt    780
ggcgttccgg cgatgtttgt taacggtaaa tatcagctga atccgcaggg tatggatacc   840
agcaatatgg atgttttgt tcagcagtat gctgatacag tgaaatatct gtccgagaaa    900
aaacaccacc accaccacca ctaa                                          924
```

<210> SEQ ID NO 14

<211> LENGTH: 921
<212> TYPE: DNA
<213> ORGANISM: Artificial Sequence
<220> FEATURE:
<223> OTHER INFORMATION: Description of Artificial Sequence: Synthetic

<400> SEQUENCE: 14

| | |
|---|---|
| atgaagaaag gttttatgtt gtttactttg ttagcggcgt tttcaggctt tgctcaggct | 60 |
| cagaaatcag cttatgcact gggtgcctcg ctgggtcgtt acatggaaaa ctctctaaaa | 120 |
| gaacaagaaa aactgggcat caaactggat aaagatcagc tgatcgctgg tgttcaggat | 180 |
| gcatttgctg ataagagcaa actctccgac caagagatcg aacagactct acaagcattc | 240 |
| gaagctcgcg tgaagtcttc tgctcaggcg aagatggaaa agacgcggc tgataacgaa | 300 |
| gcaaaaggta aagagtaccg cgagaaattt gccaaagaga aagaagatgg taaacagtac | 360 |
| actaccctgg aaaaaccggt agctggcgcg ccgcaagtgc tggagttttt ctctttcttc | 420 |
| tgcccgcact gctatcagtt tgaagaagtt ctgcatattt ctgataatgt gaagaaaaaa | 480 |
| ctgccggaag gcgtgaagat gactaaatac cacgtcaact tcatgggtgg tgacctgggc | 540 |
| aaagatctga ctcaggcatg gctgtggcg atggcgctgg gcgtgaaga caaagtgact | 600 |
| gttccgctgt ttgaaggcgt acagaaaacc cagaccattc gttctgcttc tgatatccgc | 660 |
| gatgtattta tcaacgcagg tattaaaggt gaagagtacg acgcggcgtg aacagcttc | 720 |
| gtggtgaaat ctctggtcgc tcagcaggaa aaagctgcag ctgacgtgca attgcgtggc | 780 |
| gttccggcga tgtttgttaa cggtaaatat cagctgaatc cgcagggtat ggataccagc | 840 |
| aatatggatg tttttgttca gcagtatgct gatacagtga aatatctgtc cgagaaaaaa | 900 |
| caccaccacc accaccacta a | 921 |

<210> SEQ ID NO 15
<211> LENGTH: 918
<212> TYPE: DNA
<213> ORGANISM: Artificial Sequence
<220> FEATURE:
<223> OTHER INFORMATION: Description of Artificial Sequence: Synthetic

<400> SEQUENCE: 15

| | |
|---|---|
| atgaagaaag gttttatgtt gtttactttg ttagcggcgt tttcaggctt tgctcaggct | 60 |
| cagaaatcag cttatgcact gggtgcctcg ctgggtcgtt acatggaaaa ctctctaaaa | 120 |
| gaacaagaaa aactgggcat caaactggat aaagatcagc tgatcgctgg tgttcaggat | 180 |
| gcatttgctg ataagagcaa actctccgac caagagatcg aacagactct acaagcattc | 240 |
| gaagctcgcg tgaagtcttc tgctcaggcg aagatggaaa agacgcggc tgataacgaa | 300 |
| gcaaaaggta aagagtaccg cgagaaattt gccaaagaga aagatggtaa acagtacact | 360 |
| accctggaaa aaccggtagc tggcgcgccg caagtgctgg agttttctc tttcttctgc | 420 |
| ccgcactgct atcagtttga agaagttctg catatttctg ataatgtgaa gaaaaaactg | 480 |
| ccggaaggcg tgaagatgac taaataccac gtcaacttca tgggtggtga cctgggcaaa | 540 |
| gatctgactc aggcatgggc tgtggcgatg gcgctgggcg tgaagacaa agtgactgtt | 600 |
| ccgctgtttg aaggcgtaca gaaaacccag accattcgtt ctgcttctga tatccgcgat | 660 |
| gtatttatca acgcaggtat taaaggtgaa gagtacgacg cggcgtggaa cagcttcgtg | 720 |
| gtgaaatctc tggtcgctca gcaggaaaaa gctgcagctg acgtgcaatt gcgtggcgtt | 780 |
| ccggcgatgt ttgttaacgg taaatatcag ctgaatccgc agggtatgga taccagcaat | 840 |
| atggatgttt ttgttcagca gtatgctgat acagtgaaat atctgtccga gaaaaaacac | 900 | caccaccacc accactaa                                              918

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gagctcgaat tctctagatt aaagaggaga aaggtaccca tgatgaagaa aggttttat        59

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
atgaagaaag gttttatgtt gtttactt                                         28

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
aagcctgaaa acgccgctaa caaagtaaac aacataaaac ctt                        43

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gttagcggcg ttttcaggct tgctcaggc tgctgaagct gca                         43

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
tgtcagcagc tgtagcaggt tttgcagctt cagcagcctg agc                        43

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21

-continued aacctgctac agctgctgac agcaaagcag cgttcaaaaa tga                43

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
tgcataagct gatttctgat cgtcattttt gaacgctgct ttg                43

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
gatcagaaat cagcttatgc actgggtgcc tcgctgggtc gtt                43

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
tcttttagag agttttccat gtaacgaccc agcgaggcac cca                43

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
catggaaaac tctctaaaag aacaagaaaa actgggcatc aaa                43

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
cgatcagctg atctttatcc agtttgatgc ccagtttttc ttg                43

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
tggataaaga tcagctgatc gctggtgttc aggatgcatt tgc                43

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 28
gtcggagagt tgctcttat cagcaaatgc atcctgaaca cca                   43

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 29
gataagagca aactctccga ccaagagatc gaacagactc tac                   43

<210> SEQ ID NO 30
<211> LENGTH: 43
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 30
ttcacgcgag cttcgaatgc ttgtagagtc tgttcgatct ctt                   43

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 31
agcattcgaa gctcgcgtga agtcttctgc tcaggcgaag atg                   43

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 32
cgttatcagc cgcgtctttt tccatcttcg cctgagcaga aga                   43

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 33
aaaaagacgc ggctgataac gaagcaaaag gtaaagagta ccg                   43

<210> SEQ ID NO 34
<211> LENGTH: 43
<212> TYPE: DNA
<213> ORGANISM: Artificial Sequence
<220> FEATURE:
<223> OTHER INFORMATION: Description of Artificial Sequence: Synthetic Primer

<400> SEQUENCE: 34
tttctctttg gcaaatttct cgcggtactc tttacctttt gct         43

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic Primer

<400> SEQUENCE: 35
ctgtttacca tcttcatact gcgctttctc tttggcaaat ttc         43

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic Primer

<400> SEQUENCE: 36
gtagtgtact gtttaccatc ttcatactgt ttctctttgg caaatttc    48

<210> SEQ ID NO 37
<211> LENGTH: 49
<212> TYPE: DNA
<213> ORGANISM: Artificial Sequence
<220> FEATURE:
<223> OTHER INFORMATION: Description of Artificial Sequence: Synthetic Primer

<400> SEQUENCE: 37
cagggtagtg tactgtttac catcttcata tttctctttg gcaaatttc   49

<210> SEQ ID NO 38
<211> LENGTH: 46
<212> TYPE: DNA
<213> ORGANISM: Artificial Sequence
<220> FEATURE:
<223> OTHER INFORMATION: Description of Artificial Sequence: Synthetic Primer

<400> SEQUENCE: 38
cagggtagtg tactgtttac catcttcttt ctctttggca aatttc      46

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic Primer

<400> SEQUENCE: 39
cagggtagtg tactgtttac catctttctc tttggcaaat ttc         43

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
gaaatttgcc aaagagaaag cgcagtatga agatggtaaa cag          43

<210> SEQ ID NO 41
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
gaaatttgcc aaagagaaac agtatgaaga tggtaaacag tacactac      48

<210> SEQ ID NO 42
<211> LENGTH: 49
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
gaaatttgcc aaagagaaat atgaagatgg taaacagtac actaccctg     49

<210> SEQ ID NO 43
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
gaaatttgcc aaagagaaag aagatggtaa acagtacact accctg        46

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
gaaatttgcc aaagagaaag atggtaaaca gtacactacc ctg           43

<210> SEQ ID NO 45
<211> LENGTH: 54
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
tttttaagct tttagtggtg gtggtggtgg tgttttttct cggacagata tttc    54